United States Patent
Oh et al.

(10) Patent No.: US 7,232,880 B2
(45) Date of Patent: Jun. 19, 2007

(54) MUTANT IGFBP-3 MOLECULES THAT DO NOT BIND TO IGFS, BUT RETAIN THEIR ABILITY TO FUNCTIONALLY BIND IGFBP-3 RECEPTOR

(75) Inventors: Youngman Oh, Beaverton, OR (US); Ron G. Rosenfeld, Los Altos, CA (US); Caroline K. Buckway, Tualatin, OR (US)

(73) Assignee: Oregon Health & Science University, Portland, OR (US)

( * ) Notice: Subject to any disclaimer, the term of this patent is extended or adjusted under 35 U.S.C. 154(b) by 120 days.

(21) Appl. No.: 10/415,398

(22) PCT Filed: Oct. 29, 2001

(86) PCT No.: PCT/US01/48436

§ 371 (c)(1),
(2), (4) Date: Dec. 29, 2003

(87) PCT Pub. No.: WO02/34916

PCT Pub. Date: May 2, 2002

(65) Prior Publication Data

US 2005/0069873 A1    Mar. 31, 2005

Related U.S. Application Data

(60) Provisional application No. 60/244,162, filed on Oct. 27, 2000.

(51) Int. Cl.
*A61K 38/00* (2006.01)
(52) U.S. Cl. ........................ 530/324; 530/350
(58) Field of Classification Search ................ 530/324, 530/350
See application file for complete search history.

(56) References Cited

U.S. PATENT DOCUMENTS

2004/0253689 A1    12/2004    Rechler

OTHER PUBLICATIONS

IGFBP-3 protein (*Homo sapien*) sequence from GenBank. Accession code: P17936; deposited Nov. 1, 1990.*

Christiansen et al. "The role of the MoFe protein alpha-125-Phe and beta-235-Phe residues in Azotobacter vinelandii MoFe protein Fe protein interaction". Journal of Inorganic Biochemistry. 2000. vol. 80, pp. 195-204.*
Sorlie et al. "Mechanistic features and structure of the nitrogenase alpha-Gln-195 MoFe protein". Biochemistry. 2001. vol. 40, pp. 1540-1549.*
Buckway et al., Mutation of Three Critical Amino Acids of the N-Terminal Domain of IGF-Binding Protein-3 Essential for High Affinity IGF Binding, J. Clin. Endocrinology & Metabolism 86(10):4943-4950, 2001.
Imai et al., Substitution for hydrophobic amino acids in the N-terminal domains of IGFBP-3 and -5 markedly reduce IGF-I binding and alter their biologic actions, J. Biol. Chem. 275(24):18188-18194, 2000.
Kalus et al., Structure of the IGF-binding domain of the insulin-like growth factor-binding protein-5 (IGFBP-5): implications for IGF and IGF-1 receptor interactions, Embo J. 17(22):6558-6572, 1998.
Hashimoto et al., Binding Sites and Binding Properties of Binary and Ternary Complexes of Insulin-like Growth Factor-II (IGF-II), IGF-binding Protein-3, and Acid-labile Subunit, J. Biol. Chem. 272(44):27936-27942, 1997.
Hwa et al., The Insulin-Like Growth Factor-Binding Protein (IGFBP) Superfamily, Endocrine Reviews 20(6):761-787, 1999.
Baxter, Robert C., Insulin-like growth factor (IGF)-binding proteins: interactions with IGFs and intrinsic bioactivites, Am. J. Physiol. Endocrinol. Metab. 278:E967-E976, 2000.

* cited by examiner

*Primary Examiner*—Robert A. Wax
*Assistant Examiner*—Suzanne M. Noakes
(74) *Attorney, Agent, or Firm*—Barry L. Davison; Davis Wright Tremaine

(57) ABSTRACT

There is disclosed movel mutant IGFBP-3 polypeptides and fragments thereof that have either no binding, or diminished binding to IGFs, yet retain their ability to bind to the human IGFBP-3 receptor ("P4.33"). The present invention provides novel mutant IGFBP-3 nucleic acid sequences, and expression systems. Additional embodiments provide for screening assays for identifying IGFBP-3 receptor antagonists or agonists, methods for modulating IGF-independent IGFBP-3 responses of cells expressing IGFBP-3 receptors, A methods for inducing or potentiating apoptosis of cells expressing IGFBP-3 receptors, methods for treating solid tumors having cells expressing IGFBP-3 receptors, and compositions comprising polypeptides having either no binding, or diminished binding to IGFs, yet retain their ability to bind to the IGFBP-3 receptor.

6 Claims, 17 Drawing Sheets

Figure 3
PRIOR ART

Hydrophobic patch residues on IGFBP-3 substituted with nonhydrophobic residues produced >1000 fold reduction in IGF-I affinity.

Arginine 75 → Serine

Proline 76 → Alanine

Leucine 77 → Serine

Leucine 80 → Glutamine

Leucine 81 → Glycine

Amino Acid Mutations

Wild-type
Isoleucine (I)     large nonpolar
Leucine (L)        large nonpolar

Mutant forms
Valine (V)         large nonpolar  (conserved)
Glycine (G)        small polar     (nonconserved)

IGFBP-3 Mutants Binding to IGFBP-3 Receptor: Transient Transfection of Hs578T cells with EGFP:4-33 (BP-3 receptor) Cell Lysates IPed with αGFP and Mutants

MUTANT IGFBP-3 MOLECULES THAT DO NOT BIND TO IGFS, BUT RETAIN THEIR ABILITY TO FUNCTIONALLY BIND IGFBP-3 RECEPTOR

CROSS REFERENCE TO RELATED APPLICATIONS

This application claims priority to U.S. Provisional Patent Application Ser. No. 60/244,162, filed 27 Oct. 2000.

TECHNICAL FIELD OF THE INVENTION

The present invention provides novel mutant IGFBP-3 molecules having utility in drug candidate screening assays, and therapeutic methods and compositions for the treatment of cancer and bone growth. The present invention further provides mutant IGFBP-3 cDNA sequences, and mutant IGFBP-3 polypeptides and fragments thereof. This work was supported by grants from the NIH (CA-58110, DK-51513 and 5T32 HD07497), and the Department of Defense (17-96-1-6304 and 17-97-1-7204).

BACKGROUND OF THE INVENTION

The insulin-like growth factor (hereinafter "IGF") signaling system (hereinafter "IGF axis") is comprised of the ligands IGF-I, IGF-II and insulin, and a family of transmembrane receptors including the insulin type 1- and type 2-IGF receptors (Daughaday and Rotwein, *Endocr. Rev.* 10:68-9, 1989; Werner et al., Insulin-like growth factors: Molecular and Cellular Aspects, CRC Press, LeRoith (eds.), Boca Raton, pp. 17-47, 1991.

The IGF axis also includes the insulin-like growth factor binding proteins (hereinafter "IGFBPs"). Six IGFBPs have been identified, cloned and sequenced (Baxter & Martin, *Prog. Growth Factor Res.* 1:49-68, 1989; Rosenfeld et al., *Recent Progress Hormone Res.* 46:99-159, 1991; Shimasaki & Ling, *Prog. Growth Factor Res.* 3:243-266, 1991). They share a high degree of similarity in their primary protein structure, particularly in the corresponding N- and C-terminal regions (58% and 34% similarity, respectively), which are separated by a variable mid-protein segment of 55 to 95 amino acid residues (Shimasaki & Ling, supra). The IGFBPs bind IGF-I and IGF-II, but not insulin, with high affinity (Jones & Clemmons, *Endocr. Rev.* 16:3-34, 1995). The IGFBPs appear to serve essential functions of transporting the IGFs, prolonging IGF half-lives, and regulating the availability of free IGFs for interaction with IGF receptors.

Thus, the IGFBPs modulate the effects of IGFs on growth and differentiation (Jones & Clemmons, supra; Lowe, Insulin-like growth factors: Molecular and Cellular Aspects, CRC Press, LeRoith (eds.), Boca Raton, pp. 49-85, 1991; Oh et al., *Growth Regul.* 3: 113-123, 1993; Kelley et al., *Int. J. Biochem. Cell Biol.* 28:619-637, 1993; Rajaram et al., *Endocr. Rev.* 18:801-831, 1997). Some IGFBPs (e.g., IGFBP-3) may also act as growth-suppressing factors in various cell systems through IGF-independent mechanisms (Oh, *Endocrine.* 7:111-113, 1997; Oh, *Breast Cancer Res. Treat.* 47:283-293, 1998).

Additional potential IGF binding proteins, referred to as IGFBP related proteins (hereinafter "IGFBP-rPs"), have been recently identified that have a significant similarity to the IGFBPs in their N-terminal domains (Hwa et al., *Acta Ped. Scand.* 428:37-45, 1999). Collectively, current data supports the broad concept of an "IGFBP superfamily" with both high- and low-affinity members, wherein at least some members influence cell growth and differentiation by both IGF-dependent and IGF-independent means (Hwa et al., supra; Baxter et al., *Endocrinology* 139:4036, 1998; Baxter et al., *J. Clin. Endocrinol. Metab.* 83:3213, 1998).

The human IGFBP superfamily is currently comprised of six high-affinity species (IGFBPs 1-6), and nine low-affinity IGFBP-related proteins (IGFBP-rPs). Structural characteristics of various members of the human IGFBP superfamily are summarized in Table 1.

TABLE II

Structural Characteristics of the Human IGFBP Superfamily

| IGFBP | Molecular Weight | Number of amino acids | Number of cysteines | N-linked glycosylation | Chromosomal localization | mRNA size (kb) |
|---|---|---|---|---|---|---|
| High affinity IGFBP related proteins | | | | | | |
| IGFBP-1 | 25,271 | 234 | 18 | No | 7p | 1.6 |
| IGFBP-2 | 31,355 | 289 | 18 | No | 2q | 1.5 |
| IGFBP-3 | 28,717 | 264 | 18 | Yes | 7p | 2.4 |
| IGFBP-4 | 25,957 | 237 | 20 | Yes | 17q | 1.7 |
| IGFBP-5 | 28,553 | 252 | 18 | No | 2q | 1.7, 6.0 |
| IGFBP-6 | 22,847 | 216 | 16 | No | 12 | 1.1 |
| Low affinity IGFBP related proteins | | | | | | |
| IGFBP-rP1 | ? | 251 | 18 | Yes | 4q | 1.1 |
| IGFBP-rP2 | ? | 349 (pre) | 39 | Yes | 6q | 2.4 |
| IGFBP-rP3 | ? | 357 (pre) | 41 | ? (No) | 8q | 2.4 |
| IGFBP-rP4 | ? | 379 (pre) | 35 | ? (No) | ? | 2.4 |

IGFBP-3 is the principal IGFBP in adult serum, where it circulates as a 150 kDa-complex consisting of IGFBP-3, an acid-labile subunit, and IGF peptide (Neely et al., *Acta Pediatr. Scand.* 372:116-123, 1991; Oh et al., *Growth Regul.* 3:113-123, 1993; Ruoslahti & Pierschbacher, *Science* 238: 491-493, 1987). Its principal role has been postulated to be transporting IGFs and protecting them from rapid clearance and/or degradation (Hintz & Liu, *J. Clin. Endocrinol. Metab.* 45:988-982, 1977; Baxter et. al., *Biochem. Biophys. Res. Commun.* 139:1256-1259, 1986; Baxter & Martin, *Prog. Growth Factor Res.* 1:49-56, 1989).

The IGF Axis in the Human Mammary System

IGF-I, IGF-II, type-1 and type-2 IGF Receptors, and the IGFBPs. The IGFs are major regulators of mammary epithelial and breast cancer cell growth (Jones & Clemmons, *Endocr. Rev.* 16:3-34, 1995; Oh, *Endocrine.* 7:111-113, 1997; Oh, *Breast Cancer Res. Treat.* 47:283-293, 1998; De Leon et al., *Growth Factors* 6:327-336, 1992; Furlanetto & DiCarlo, *Cancer Res.* 44:2122-2128, 1984; Huff et al., *Cancer Res.* 46:4613-4619, 1986). IGF-I and IGF-II, for example are potent mitogens for a number of breast cancer cell lines in vitro (De Leon et al., supra; Huff et al., supra; Westley & May, *Reviews on Endocrine-Related Cancer* 39:29-34, 1991; Baxter et al., Insulin-like Growth Factors/Somatomedins, De Gruyter, Spencer (ed.), Berlin, pp615-618, 1983). Moreover, IGF-I and IGF-II mRNAs are detectable in the majority of human breast tumor specimens (Cullen et al., *Cancer Res.* 51:4978-4985, 1991; Paik, *Breast Cancer Res. Treat.* 22:31-38, 1992). Virtually all breast tumor specimens, and cell lines derived therefrom, express and produce type-1 and type-2 IGF receptors, and insulin receptors (Cullen et. al., *Cancer Res.* 50:48-53, 1990; Bonneterre et al., *Cancer Res.* 50:6931-6935, 1990; Peyrat & Bonneterre, *Breast Cancer Res. Treat.* 22:59-67, 1992; De Leon et. al., *Biochem. Biophys. Res. Commun.* 152:398-405, 1988). The mitogenic effects of both IGF-I and IGF-II are mediated by the type-1 IGF receptor, as determined through the use of estrogen-dependent breast cancer cells (De Leon et al., *Growth Factors* 6:327-336, 1992; Papa et. al, *Mol. Endocrinol.* 5:709-717, 1991).

In contrast, relatively little is known about the molecular mechanisms and biological functions of the IGFBPs in the context of breast cancer. Specifically, breast cancer cells are known to secrete various types of IGFBPs, and these appear to regulate the availability of free IGFs for interaction with IGF receptors (Lamson et al., *Growth Factors* 5:19-28, 1991). The predominant secreted IGFBP appears to correlate with the estrogen receptor status of the cell (Figueroa et al., *J. Cell. Biochem.* 52:196-205, 1993). Estrogen-nonresponsive (estrogen receptor (ER)-negative) cells secrete predominantly IGFBP-3 and IGFBP-4 as major species, and IGFBP-6 as a minor one. Estrogen-responsive ER-positive) cells secrete IGFBP-2 and IGFBP-4 as major species, and IGFBP-3 and IGFBP-5 as minor ones.

Therefore, the IGF axis in breast cancer is complex, involving autocrine, paracrine, or endocrine-derived IGFs that bind to specific cellular receptors and thereby elicit, inter alia, IGFBP secretion by the target cells. The IGFBPs, in turn, appear to regulate the availability of free IGFs for interaction with IGF receptors. However, the broader biological significance of IGFBPs generally, or in the particular context of breast cancer is unclear. Moreover, the basis and significance of variations in IGFBP secretory specificity are unknown, and the predominant species may vary significantly depending on the estrogen responsivess of the secreting cells.

IGFBP-3 and its anti-proliferative action in human breast cancer cells. Expression of IGFBP-3 in human breast cancer cells is hormonally regulated, and IGFBP-3 is known to inhibit cancer cell growth through both (a) IGF-dependent, and (b) IGF-independent mechanisms.

(a) IGF-dependent anti-proliferative action. IGFBP-3 is known to indirectly inhibit cancer cell growth through IGF-dependent interactions. IGFBP-3 is the predominant IGF-binding protein in human serum where it circulates as part of a 150 kDa ternary complex. The binding affinity of IGFBP-3 for IGF peptides is generally higher than that of the type I and type II IGF cell-surface receptors, implying that IGFBP-3 can modulate IGF binding to its receptor, thereby blocking local IGF-dependent biological action. In fact, co-incubation of cells with IGFBP-3 and IGF peptides results in an inhibition of the IGF-dependent mitogenic effect in human breast cancer cells, in vitro (Martin et al., *Endocrinology* 136:1219-1226, 1995). In situ hybridization studies of the expression of IGF-I and IGF-II in human breast cancer tissues indicate that IGF-I mRNA is detected only in stromal cells, and not in normal or malignant epithelial cells implying that IGF-I may function as a paracrine stimulator of epithelial cells. In contrast, IGF-II mRNA was expressed in both malignant epithelial cells and their adjacent stromal cells (Paik, *Breast Cancer Res. Treat.* 22:31-38, 1992). Both paracrine or autocrine effects of IGF peptides can be modulated in vivo by IGFBP-3 produced by epithelial cells.

This IGF-dependent mechanism for IGFBP-3 inhibition of cancer cell growth is consistent with IGFBP-3 proteolysis studies. Post-translationally, IGFBP-3 can be proteolyzed by proteases such as cathepsin D, prostate-specific antigen (PSA) and plasmin, that are detectable in human breast cancer cells (Capony et. al., *Cancer Res.* 49:3904-3909, 1989; Conover & De Leon, *J. Biol. Chem.* 269:7076-7080, 1994; Yuet et al., *Clinical Biochem.* 27:75-79, 1994; Cohen et al., *J. Clin. Endocrinol. Metab.* 75:1046-1053, 1993; Schmitt et al., *Biomedica Biochemica Acta* 50:731-741, 1991; Lee et al., *J. Clin. Endocrinol. Metab.* 79: 1376-1382, 1994). In general, IGFBP-3 proteases are postulated to lower the affinity of IGFBP-3 for IGF, thereby increasing the availability of IGFs to cell-membrane receptors. PSA, for example, has been shown to reverse the inhibitory effect of IGFBP-3 on IGF-stimulated prostate cell growth by cleaving IGFBP-3 and generating IGFBP-3 fragments with lower affinity for IGFs (Cohen et al., *J. Clin. Endocrinol. Metab.* 73:401-407, 1991). However, the broad biological significance and molecular actions of IGFBP-3 proteolysis are unclear in the context of human breast cancer.

(b) IGF-independent anti-proliferative action. IGFBPs may also have specific IGF-independent biological effects in various cell systems, including human breast cancer cells. For example, exogenously added IGFBP-3 (in the absence of added IGF) inhibits estrogen-stimulated breast cancer cell proliferation (Pratt & Pollak, *Biochem. Biophys. Res. Commun.* 198:292-297, 1994). Moreover, estrogen can inhibit expression and secretion of IGFBP-3, whereas anti-estrogens (e.g., tamoxifen and ICI 182,780) stimulate production of IGFBP-3 in ER-positive human breast cancer cells.

Likewise, the expression and production of IGFBP-3 is specifically stimulated by TGF-β and retinoic acid ("RA") in human breast cancer cells, consistent with a possible role for IGFBP-3 in TGF-β- and RA-induced growth inhibition (Martin et al., *Endocrinology* 136:1219-1226, 1995; Fontana et al., *Endocrinology* 128:1115-1122, 1991; Oh et al., *J. Biol. Chem.* 270:13589-13592, 1995). The anti-proliferative effects of TGF-β, RA, TNF-α and vitamin-D analogs in human breast cancer cells appear to be partially mediated through the IGFBP-3 axis (Oh et al., supra; Gucev et al., *Cancer Research*, 56:1545-50, 1996; Rozen et al., *Int. J. Oncol.* 13: 865-869, 1998; Colston et al., *J. Mol. Endocrinol.* 20: 157-162, 1998).

Other studies also support the function of IGFBP-3 as a major IGF-independent growth-suppressing factor in various cell systems. See Valentinis et al., *Mol. Endocrinol.* 9: 361-367, 1995 (showing that growth rate is significantly reduced in IGFBP-3-transfected fibroblasts with a targeted disruption of the IGF-I receptor gene); Delbe et al., *Biochem. Biophys. Res. Commun.* 179: 495-501, 1991 (showing that purified mouse IGFBP-3 binds to the chick embryo fibroblast cell surface and inhibits cell growth); Andreatta-Van Leyen et al., *J. Cell Physiol.* 160: 265-274, 1994 (showing that up-regulation of IGFBP-3 expression is correlated with RA-induced cell growth inhibition in cervical epithelial cells); and Buckbinder et al., *Nature* 377: 646-649, 1995 (showing that the tumor suppressor p53 induces IGFBP-3 expression, indicating that IGFBP-3 may be a mediator in p53 signaling).

Additonal studies support the ability of IGFBP-3 to induce apoptosis. For example, in MCF-7 cells, the treatment with recombinant human IGFBP-3 for 72 hours has been shown to increase apoptosis and to inhibit [$^3$H]-thymidine incorporation (Nickerson et al., *Biochem. Biophys. Res. Commun.* 237:690-693, 1997). In Hs578T human breast cancer cells, IGFBP-3 results in no direct induction of apoptosis, but preincubation of the cells with IGFBP-3 caused a dose-dependent potentiation of apoptosis by ceramide, an apoptosis-inducing agent, consistent with an IGF-independent activity of IGFBP-3 (Gill et al., *J. Biol. Chem.* 272:25602-25606, 1997).

Therefore, IGFBP-3 is an important IGF-independent anti-proliferative factor for human breast cancer cells.

The IGF Axis in Human Chondrocyte Proliferation and Differentiation

Endochondral bone development results from the condensation and proliferation of mesenchymal cells, which in turn, mature into differentiated and terminally differentiated chondrocytes, forming cartilaginous templates that are subsequently replaced by bone. During the process of chondrocyte proliferation and differentiation ("chondrogenesis"), chondrocytic cells progress through an ordered program of proliferation and differentiation. This program is strictly regulated, so that proper bone length is maintained. Several hormones and growth factors have been demonstrated to regulate differentiation rate through antiproliferative and/or apoptotic mechanisms (Serra et al., *J. Cell. Biol.* 139:541-552, 1997; Deng et al., *Cell* 84:911-921, 1996; Kronenberg et al., *Recent Prog. Horm. Res.* 53:283-303, 1998).

Insulin-like growth factors (IGFs) have been shown to play a central role in chondrogenesis (Spagnoli & Rosenfeld *Endocrinol Metab. Clin. North Am.* 25:615-631, 1996). IGFBP-3 sequesters IGF, inhibiting binding to the IGF-I receptor, and in some cell systems also has a direct (i.e., IGF-independent) effect on cell replication. However, the functional relationship between IGF and IGFBP-3 in endochondral bone growth is not well understood.

IGFBP-3 Receptor ("P4.33")

Finally, it is known that IGFBP-3 can bind to the cell surface and act as a growth inhibitor for ER-negative human breast cancer cells (Oh et al., *J. Biol. Chem.* 270:13589-13592, 1995). The interaction of IGFBP-3 with the breast cancer cell surface and its subsequent biological effects appear to involve IGFBP-3-specific cell surface association proteins that may mediate the direct inhibitory effect of IGFBP-3 on the growth of cells in monolayer (Oh et al., *J. Biol. Chem.* 268:26045-26048, 1993).

The present applicants previously identified and characterized a novel protein, P4.33, that interacts specifically with IGFBP-3 in an IGF-independent manner (see International Patent Application PCT/US01/16437, incorporated by reference herein in its entirety). P4.33 functions as a receptor for IGFBP-3, and is thereby involved in the inhibition of DNA synthesis and cellular proliferation, and in the induction of apoptosis in cancer cells.

However, because IGFBP-3 acts in vivo and in vitro as a bivalent molecule, binding to both IGF and to P4.33 (i.e., modulates cancer cell growth and apoptosis via both IGF-dependent and independent mechanisms), assessing the physiological properties of potential therapeutic compounds is complex and troublesome. A modulator (e.g., antagonist) of the IGFBP-3/P4.33 interaction might act indirectly (i.e., allosterically) through interaction at the IGF binding site of IGFBP-3, rather than by directly antagonizing the P4.33 lingand-binding site. Thus, screening assays based on modulating the IGFBP-3/P4.33 binding interaction would identify, in addition to those compounds that affect IGF-independent processes (because they directly interact with IGFBP-3/P4.33 complex), compounds that affect IGF-dependent processes via interaction with the IGF binding site of IGFBP-3.

Therefore, there is a need in the art for effective screening assays for the identification of specific antagonists and agonists of P4.33 (i.e. to identify specific antagonist and agonists of IGF-independent processes). There is a need in the art to identify novel methods and compositions for the treatment of cancer, and cartilage and bone disorders. There is a need in the art to further understand the role of IGFBP-3 in condrogenesis and bone growth. There is a need in the art to identify novel IGFBP-related polypeptides that have no, or diminished binding to IGFs, but retain affinity for the IGFBP-3 receptor.

SUMMARY OF THE INVENTION

This present invention provides novel mutant IGBP-3 molecules that do not bind to IGFs, but retain their ability to functionally bind P4.33. The present invention provides, inter alia, for an isolated nucleic acid comprising a sequence that encodes a polypeptide comprising an amino acid sequence selected from the group consisting of the amino acid sequences of SEQ ID NOS:3-10, or of consecutive residues 54-87 thereof, wherein the polypeptide binds to the extracellular domain of the human IGFBP-3 receptor. Preferably, the encoded polypeptide is from about 87 to about 264 amino acids in length. Preferably, the encoded polypeptide is, or comprises a recombinant variant of human IGFBP-3.

The present invention also provides for an expression vector comprising the above-described nucleic acids operably linked to an expression control sequence, and for cultured cells comprising the expression vector.

Additional embodiments provide for purified polypeptides, the amino acid sequence of which comprises an amino acid sequence selected from the group consisting of the amino acid sequences of SEQ ID NOS:3-10, or of consecutive residues 54-87 thereof wherein the polypeptide binds to the extracellular domain of the human IGFBP-3 receptor. Preferably, the purified polypeptides are from about 87 to about 264 amino acids in length. Preferably, the purified polypeptides are, or comprises recombinant variants of human IGFBP-3.

Particular embodiments of the present invention provide a method of identifying an IGFBP-3 receptor antagonist or agonist, the method comprising: providing a first polypeptide comprising the ligand-binding domain of the human IGFBP-3 receptor; contacting the first polypeptide with a test compound and with a second polypeptide, the amino acid sequence of which comprises an amino acid sequence selected from the group consisting of the amino acid sequences of SEQ ID NOS:3-10, or of consecutive residues 54-87 thereof, wherein the polypeptide binds to the extracellular domain of the human IGFBP-3 receptor; and determining whether binding of the second polypeptide to the first polypeptide is decreased or increased in the presence of the test compound, where a decrease or increase in said binding indicates that the test compound is an IGFBP-3 receptor antagonist or agonist, respectively. Preferably, determining whether binding of the second polypeptide to the first polypeptide is decreased or increased in the presence of the test compound comprises: contacting the test compound with the first polypeptide and the second polypeptide, wherein at least one of the polypeptides bears a detectable label; and assaying any resulting first polypeptide/second polypeptide complex for the presence of the label. Preferably, the detectable label is a radiolabel, a fluorescent reporter or quencher moiety, an enzymic label that catalyzes a colorometric or fluorometric change, or combinations thereof Preferably, either the first polypeptide or the second polypeptide is immobilized onto a solid phase. Preferably, the second polypeptide is from about 87 to about 264 amino acids in length. Preferably, the second polypeptide is, or comprises a recombinant variant of human IGFBP-3.

The present invention also provides for method of identifying an IGFBP-3 receptor antagonist or agonist, the method comprising: providing a cell that expresses the human IGFBP-3 receptor, or its ligand-binding domain on its surface; contacting the cell with a test compound and a polypeptide, the amino acid sequence of which comprises an amino acid sequence selected from the group consisting of the amino acid sequences of SEQ ID NOS:3-10, or of consecutive residues 54-87 thereof, wherein the polypeptide binds to the extracellular domain of the human IGFBP-3 receptor; and determining whether binding of the polypeptide to the human IGFBP-3 receptor, or its ligand-binding domain is decreased or increased in the presence of the test compound, where a decrease or increase in said binding indicates that the test compound is an IGFBP-3 receptor antagonist or agonist, respectively. Preferably, the polypeptide is from about 87 to about 264 amino acids in length. Preferably, the polypeptide is, or comprises a recombinant variant of human IGFBP-3. Preferably, determining whether binding of the polypeptide to the human IGFBP-3 receptor, or its ligand-binding domain is decreased or increased in the presence of the test compound comprises a cell-based assay selected from the group consisting of cell growth, cell differentiation, cell migration, apoptosis, signal transduction, endocytosis, and receptor-level regulation assays. Preferably, the cell differentiation assay involves measurement of at least one of type II collagen or proteoglycan.

Further embodiments provide a method for modulating IGF-independent IGFBP-3 responses of a cell expressing a IGFBP-3 receptor, comprising contacting the cell with a polypeptide, the amino acid sequence of which comprises an amino acid sequence selected from the group consisting of the amino acid sequences of SEQ ID Nos:3-10, or of consecutive residues 54-87 thereof, wherein the polypeptide binds to the extracellular domain of the human IGFBP-3 receptor. Preferably, the polypeptide is from about 87 to about 264 amino acids in length Preferably, the polypeptide is, or comprises a recombinant variant of human IGFBP-3. Preferably, the cell is a cancer cell, a mesenchymal cell, or a chondrocyte. Preferably, the cancer cell is a breast cancer cell, small-cell lung carcinoma cell, ovarian cancer cell, or colon cancer cell.

In particular embodiments, there is provided a method for inducing or potentiating apoptosis of a cell expressing a IGFBP-3 receptor, comprising contacting the cell with a polypeptide, the amino acid sequence of which comprises an amino acid sequence selected from the group consisting of the amino acid sequences of SEQ ID Nos:3-10, or of consecutive residues 54-87 thereof, wherein the polypeptide binds to the extracellular domain of the human IGFBP-3 receptor. Preferably, the polypeptide is from about 87 to about 264 amino acids in length. Preferably, the polypeptide is, or comprises a recombinant variant of human IGFBP-3. Preferably, the cell is a cancer cell, a mesenchymal cell, or a chondrocyte. Preferably, the cancer cell is a breast cancer cell, small-cell lung carcinoma cell, ovarian cancer cell, or colon cancer cell.

The present invention also provides a method for treating a solid tumor having cells expressing a IGFBP-3 receptor, comprising contacting the cells with a polypeptide, the amino acid sequence of which comprises an amino acid sequence selected from the group consisting of the amino acid sequences of SEQ ID Nos:3-10, or of residues 54-87 thereof, wherein the polypeptide binds to the extracellular domain of the human IGFBP-3 receptor. Preferably, the solid tumor is of breast cancer, ovarian cancer, or colon cancer.

Additionally, the present invention provides a composition comprising a polypeptide, the amino acid sequence of which comprises an amino acid sequence selected from the group consisting of the amino acid sequences of SEQ ID Nos:3-10, or of residues 54-87 thereof, wherein the polypeptide binds to the extracellular domain of the human IGFBP-3 receptor. Preferably, the polypeptide is from about 87 to about 264 amino acids in length. Preferably, the polypeptide is, or comprises a recombinant variant of human IGFBP-3.

BRIEF DESCRIPTION OF THE FIGURES

FIG. 3 shows data from Imai et al. (J. Biol. Chem. 275:18188-18194, 2000) illustrating that mutations involving 5 amino acids in IGFBP-3 (lower-half of figure), abolish IGF binding, as predicted by Kalus et al., based on the consensus hdrophobic region in BP-5, as shown if FIG. 2.

FIG. 4 shows an amino acid sequence comparison of IGFBP-3 (SEQ ID NO:11) and IGFBP-5 (SEQ ID NO:12). The "consensus," or identical amino acids are framed in boxes. Circles below certain amino acids identify those amino acids predicted to be important for IGF interaction based on the NMR studies of IGFBP-5 (Kalus et al.). The stars above particular amino acid positions, identify 3 amino acids in IGFBP-3 that were mutated according to the present invention. Disulfide bonds are connected with brackets.

FIG. 5 shows, according to the present invention, amino acid changes made to IGFBP-3 using site-directed mutagenesis. The size and polarity of the corresponding relevant amino acids are noted at the right. Valine was used as a conservative replacement, whereas, glycine was used as a nonconserved replacement.

DETAILED DESCRIPTION OF THE INVENTION

Definitions

Figure 1:
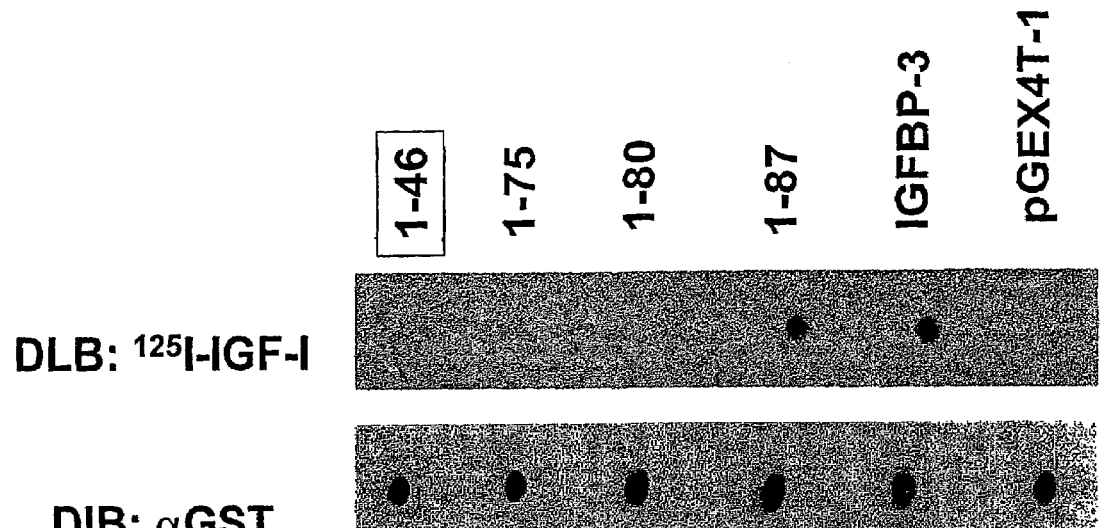
FIG. 1 shows the $[^{125}I]$-IGF-I binding affinity of IGFBP-3 N-terminal deletion fragments. The binding of these recombinant IGFBP-3 "deletion" fragments to $[^{125}I]$-IGF-I is shown, along with that of wild-type IGFBP-3 binding, and control vector (pGEX4T-1). The $[^{125}I]$-IGF-I binding was abolished in all cases except for the 1-87 fragment, and wild type (Example 2, below).

The following terms as used herein shall have the meaning indicated:

"P4.33" (IGFBP-3 receptor) means P4.33 gene products, such as transcripts and the P4.33 receptor, protein, polypeptides or fusion proteins (PCT/US01/16437). Polypeptides or peptide fragments of the P4.33 are referred to as P4.33 polypeptides or P4.33 peptides. Fusions of P4.33, or P4.33 polypeptides, or peptide fragments to an unrelated protein are referred to herein as P4.33 fusion proteins. A functional P4.33 refers to a protein that binds IGFBP-3, or IGFBP-3 peptides in vivo or in vitro.

"P4.33 nucleotides" or coding sequences: means DNA sequences encoding P4.33 mRNA transcripts, P4.33 protein, polypeptide or peptide fragments of P4.33, or P4.33 fusion proteins. P4.33-nucleotide sequences encompass DNA, including genomic DNA (e.g., the P4.33 gene) or cDNA.

"Anti-P4.33 antibody" means an antibody, or binding fragment thereof, that binds to (i.e., that recognizes one or more P4.33 epitopes of) a P4.33 receptor, protein, or polypeptide, or to a P4.33 fusion protein through interaction with, at least in part, P4.33 epitopes of said fusion protein. Anti-P4.33 antibodies include, but are not limited to, double-chain, single-chain, Fab fragments, F(ab')$_2$ fragments, anti-idiotypic antibodies, polyclonal, monoclonal, chimeric, humanized antibodies, and P4.33 eptiope-binding fragments of any of the foregoing.

"IGFBP-3" means "Insulin-like Growth Factor Binding Protein-3," IGFBP-3 gene products, e.g., transcripts and the IGFBP-3 protein. Polypeptides or peptide fragments of the IGFBP-3 are referred to as IGFBP-3 polypeptides or IGFBP-3 peptides. Fusions of IGFBP-3, or IGFBP-3 polypeptides, or peptide fragments to an unrelated protein are referred to herein as IGFBP-3 fusion proteins. A functional IGFBP-3 refers to a protein that binds P4.33, or P4.33 peptides in vivo or in vitro.

"IGFBP-3 mutant" means "Insulin-like Growth Factor Binding Protein-3 mutant," IGFBP-3 mutant gene products, e.g., transcripts and the IGFBP-3 mutant protein. Mutant polypeptides or peptide fragments of IGFBP-3 are referred to as mutant IGFBP-3 polypeptides or mutant IGFBP-3 peptides. Fusions of mutant IGFBP-3, or IGFBP-3 polypeptides, or peptide fragments to an unrelated protein are referred to herein as mutant IGFBP-3 fusion proteins. A functional mutant IGFBP-3 of the present invention refers to a protein that binds P4.33, or P4.33 peptides in vivo or in vitro, but shows decreased binding of IGFs relative to wild-type protein.

"Hs578T cells" are art-recognized human breast cancer cell lines;

"COS-7 cells" refer to the art-recognized human cell line;

"RCJ3.1C5.18 cells" refer to the art-recognized chondrogenic cell line obtained from Dr. Jane E. Aubin (University of Toronto).

"FLAG" means "the art-recognized FLAG epitope tag";

"GST" means "glutathione S-transferase."

Overview

The present invention relates to the biological role of IGFBP-3 in regulating cell growth and differentiation. Particular embodiments provide for novel mutant IGFBP-3 molecules that have either no binding, or show reduced binding to IGFs, yet retain their ability to bind to P4.33 (IGFBP-3 receptor). Additional embodiments provide novel mutant IGFBP-3 nucleic acid sequences, and novel mutant IGFBP-3 polypeptides and fragments thereof The present invention further provides novel drug candidate screening assays, and diagnostic and therapeutic methods and compositions for the treatment of cancer and tumor suppression, utilizing mutant IGFBP-3 molecules.

The invention described herein encompasses screening assays for identification of cancer therapeutic compounds. The invention also encompasses agonists and antagonists of the IGFBP-3/P4.33 interaction, including small molecules, large molecules, and antibodies, as well as nucleotide sequences that can be used to inhibit IGFBP-3 gene expression, such as antisense and ribozyme molecules. The invention also encompasses the use of such compounds to treat cancer and disorders of cartilage and bone.

In particular, cellular and non-cellular assays are described that can be used to identify compounds that interact with IGFBP-3 or P4.33 to mimic, modulate or antagonize association between these two molecules, and/or to modulate the activity of P4.33, IGFBP-3, or the P4.33:IGFBP-3 complex. The cell based assays can be used to identify compounds or compositions that affect the activity, nuclear translocation, or cellular compartmentalization of P4.33, IGFBP-3, or the P4.33:IGFBP-3 complex, whether they bind to of P4.33, IGFBP-3, or the P4.33:IGFBP-3 complex or act on intracellular factors involved in the downstream signal transduction pathway. Such cell-based assays of the invention utilize cells, cell lines, or engineered cells or cell lines that express P4.33 and/or IGFBP-3, or fusions thereof with unrelated proteins. The cells can be further engineered to incorporate a reporter molecule linked to the signal transduced by P4.33, IGFBP-3, or the P4.33:IGFBP-3 complex to aid in the identification of compounds that modulate P4.33-mediated signaling activity.

The present invention also encompasses the use of cell-based assays, and/or cell-lysate assays (e.g., in vitro transcription or translation assays) to screen for compounds or compositions that enhance P4.33 gene expression. Such assays could be used, e.g. to screen for transcriptional or translational activators. Alternatively, engineered cells or translation extracts can be used to screen for compounds (including antisense, ribozyme and or triple-helix agents) that inhibit the translation of IGFBP-3 mRNA transcripts, and therefore, affect expression of IGFBP-3.

The invention also encompasses IGFBP-3 mutant proteins, polypeptides (including soluble IGFBP-3 mutant polypeptides or peptides) and IGFBP-3 mutant fusion proteins for use in cell, and non-cell based assays for screening compounds that interact with, and/or modulate the activity of P4.33, IGFBP-3, or the P4.33:IGFBP-3 complex for use in generating antibodies, and for diagnostics and therapeutics.

IGFBP-3 mutant protein products can be used as P4.33 antagonists or agonists to treat cancer. Such IGFBP-3 mutant-protein products include but are not limited to peptides or polypeptides corresponding to one or more IGFBP-3 mutant domains (e.g., the IGFBP-3 interaction domain), truncated IGFBP-3 mutant polypeptides lacking one or more P4.33 domains (e.g., lacking the IGF binding domain), and IGFBP-3 mutant fusion protein products (e.g., GST fusions, or eptitope tagged fusions, including EGFP and FLAG fusions). Alternatively, antibodies to the IGFBP-3 mutant that are P4.33 agonists or antagonists (including compounds that modulate signal transduction that may act on downstream targets in the P4.33 signal transduction pathway) can be used to treat cancer.

For example, the administration of an effective amount of an appropriate soluble IGFBP-3 mutant polypeptide, or a IGFBP-3 mutant fusion protein (e.g., IGFBP-3$^{H4}$) would compete with endogenous IGFBP-3 to modulate the activity of P4.33, IGFBP-3, or the P4.33:IGFBP-3 complex. In yet another approach, nucleotide constructs encoding such IGFBP-3 mutant products can be used to genetically engineer host cells to express such IGFBP-3 mutant products in vivo; these genetically engineered cells can function as "bioreactors" in the body, delivering a continuous supply of the appropriate IGFBP-3 mutant peptide, soluble IGFBP-3 mutant polypeptide, or IGFBP-3 mutant fusion protein.

"Gene therapy" approaches for the modulation of P4.33 expression and/or activity in the treatment of cancer are within the scope of the invention. For example, nucleotide constructs encoding functional P4.33 ligands, mutant P4.33 ligands can be used to regulate P4.33 expression. The invention also encompasses pharmaceutical formulations and methods for treating cancer, as well as cancer diagnostic and prognostic methods.

IGFBP-3 Mutant Proteins, Polypeptides, and Antibodies

IGFBP-3 mutant protein, polypeptides and peptide fragments, mutated, truncated or deleted forms of the IGFBP-3 mutant and/or IGFBP-3 mutant fusion proteins can be prepared for a variety of uses, including but not limited to the generation of antibodies, as reagents in diagnostic assays, the identification of other cellular gene products involved in the regulation cancer, as reagents in assays for screening for compounds that can be used in the treatment cancer, and as pharmaceutical reagents useful in the treatment of cancer.

Production of IGFBP-3 mutant Polypeptides. Peptides corresponding to one or more domains of the IGFBP-3 mutant, truncated or deleted IGFBP-3 mutant (e.g., IGFBP-3 mutant in which one or more regions or domains have been deleted) as well as fusion proteins in which the fall length IGFBP-3 mutant, a IGFBP-3 mutant peptide or truncated IGFBP-3 mutant is fused to an unrelated protein are also within the scope of the invention (e.g., GST, FLAG and EGFP fusions). Such soluble peptides, proteins, fusion proteins, or antibodies (including anti-idiotypic antibodies) that bind IGFBP-3 mutant, can be used as described herein to treat cancer. To this end, peptides corresponding to individual domains of IGFBP-3 mutant, soluble deletion mutants of IGFBP-3 mutant, or the entire IGFBP-3 mutant can be fused to another polypeptide (e.g., an IgFc polypeptide, or eptitope tag).

Such peptides, polypeptides, and fusion proteins can be prepared by recombinant DNA techniques. For example, nucleotide sequences encoding one or more IGFBP-3 mutant regions or domains can be synthesized or cloned and ligated together to encode a soluble IGFBP-3 mutant polypeptide. The DNA sequence encoding one or more IGFBP-3 mutant regions or domains can be ligated together directly or via a linker oligonucleotide that encodes a peptide spacer. Such linkers may encode flexible, glycine-rich amino acid sequences thereby allowing the domains that are strung together to assume a conformation that can bind IGFBP-3 mutant ligands. Alternatively, nucleotide sequences encoding individual regions or domains can be used to express IGFBP-3 mutant peptides.

A variety of host-expression vector systems may be utilized to express nucleotide sequences encoding the appropriate regions of the IGFBP-3 mutant to produce such polypeptides. Where the resulting peptide or polypeptide is a soluble derivative the peptide, the polypeptide can be recovered from the culture media. Where the polypeptide or protein is not secreted, the IGFBP-3 mutant product can be recovered from the host cell itself.

The host-expression vector systems also encompass engineered host cells that express the IGFBP-3 mutant or functional equivalents. Purification or enrichment of the IGFBP-3 MUTANT from such expression systems can be accomplished using appropriate methods well known to those skilled in the art. However, such engineered host cells themselves may be used in situations where it is important not only to retain the structural and functional characteristics of the IGFBP-3 MUTANT, but also to assess biological activity, e.g., in drug screening assays.

The host-expression vector systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing IGFBP-3 mutant nucleotide sequences; yeast (e.g., *Saccharomyces, Pichia*) transformed with recombinant yeast expression vectors containing the IGFBP-3 MUTANT nucleotide sequences; insect cell systems infected with recombinant virus expression vectors (e.g., baculovirus) containing the IGFBP-3 MUTANT sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing IGFBP-3 MUTANT nucleotide sequences; or mammalian cell systems (e.g., COS, CHO, BHK, 293, 3T3, MCF-7, Hs578T) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the IGFBP-3 MUTANT gene product being expressed. For example, when a large quantity of such a protein is to be produced, for the generation of pharmaceutical compositions of IGFBP-3 MUTANT protein or for raising antibodies to the IGFBP-3 MUTANT protein, vectors that direct the expression of high levels of fusion protein products that are readily purified may be desirable. Such vectors include, but are not limited, to the *E. coli* expression vector pUR278 Luther et al., *EMBO J.* 2:1791, 1983), in which the IGFBP-3 MUTANT coding sequence may be ligated individually into the vector in frame with the lacZ coding region so that a fusion protein is produced; pIN vectors (Inouye & Inouye, *Nucleic Acids Res.* 13:3101-3109, 1985; Van Heeke & Schuster, *J. Biol. Chem.* 264: 5503-5509, 1989); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

Alternatively, utilizing an antibody specific for the fusion protein being expressed may readily allow for purification any fusion protein. For example, a system described by Janknecht et al. allows for the facile purification of non- denatured fusion proteins expressed in human cell lines (Janknecht, et al., *Proc. Natl. Acad. Sci. USA* 88:8972-8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$:nitriloacetic acid-agarose columns and histidine-tagged proteins are selectively eluted with imidazole-containing buffers.

*Autographa californica* nuclear polyhedrosis virus (AcNPV) can be used as a vector to express foreign genes in an insect system. The virus grows in *Spodoptera frugiperda* cells. The IGFBP-3 MUTANT coding sequence may be cloned individually into non-essential regions (e.g., the polyhedrin gene) of the virus and placed under control of an AcNPV promoter (e.g., the polyhedrin promoter). Successful insertion of IGFBP-3 MUTANT gene coding sequence will result in inactivation of the polyhedrin gene and production of non-occluded recombinant virus (i.e., virus lacking the proteinaceous coat coded for by the polyhedrin gene). The recombinant viruses are then used to infect cells in which the inserted gene is expressed (Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the IGFBP-3 MUTANT nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the IGFBP-3 MUTANT gene product in infected hosts. (Logan & Shenk, *Proc. Natl. Acad. Sci. USA* 81:3655-3659, 1984). Specific initiation signals may also be required for efficient translation of inserted IGFBP-3 MUTANT nucleotide sequences. These signals include the ATG initiation codon and adjacent sequences. In cases where an entire IGFBP-3 MUTANTgene or cDNA, including its own initiation codon and adjacent sequences, is inserted into the appropriate expression vector, no additional translational control signals may be needed. However, in cases where only a portion of the IGFBP-3 MUTANT coding sequence is inserted, exogenous translational control signals, including, perhaps, the ATG initiation codon, must be provided. Furthermore, the initiation codon must be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (Bittner et al., *Methods Enzymol.* 153:516-544, 1987).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. Accordingly, eukaryotic host cells that possess cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, MCF-7, Hs578T and WI38 cell lines.

For long-term, high-yield production of recombinant proteins, stable expression is preferred. For example, cell lines that stably express the IGFBP-3 MUTANT sequences may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer stable cell lines that express the IGFBP-3 MUTANT gene product (e.g., the MCF-7:BP-3,#3 and #1 cell lines discussed in the Examples below). Such engineered cell lines may be particularly useful in screening and evaluation of compounds that affect the endogenous activity of the IGFBP-3 MUTANT gene product.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Low, et al., *Cell* 22:817, 1980) genes can be employed in tk$^-$, hgprt$^-$ or aprt$^-$ cells, respectively. Also, anti-metabolite resistance can be used as the basis of selection for the following genes: dhfr, that confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, that confers resistance to mycophenolic acid (Mulligan & Berg, *Proc. Natl. Acad. Sci. USA* 78:2072, 1981); neo, that confers resistance to the aminoglycoside G418 (Colberre-Garapin et al., *J. Mol. Biol.* 150:1, 1981); and hygro, that confers resistance to hygromycin (Santerre et al., *Gene* 30:147, 1984).

Antibodies to IGFBP-3 Mutant Polypeptides. Antibodies that specifically recognize one or more epitopes of IGFBP-3 MUTANT, or epitopes of conserved variants of IGFPB-3 MUTANT, or peptide fragments of the IGFBP-3 MUTANT are also encompassed by the invention. Such antibodies include but are not limited to polyclonal antibodies, monoclonal antibodies (mAbs), humanized or chimeric antibodies, single-chain antibodies, Fab fragments, F(ab')$_2$ fragments, fragments produced by a Fab expression library, anti-idiotypic (anti-Id) antibodies, and epitope-binding fragments of any of the above. The antibodies of the invention may be used, for example, in the detection of the IGFBP-3 MUTANT in a biological sample and may, therefore, be utilized as part of a diagnostic or prognostic technique whereby patients or tissue samples may be tested for abnormal amounts of IGFBP-3 MUTANT. Such antibodies may also be utilized in conjunction with, for example, compound screening schemes, as described, above, for the evaluation of the effect of test compounds on expression and/or activity of the IGFBP-3 MUTANT gene product. Additionally, such antibodies can be used in conjunction with the gene therapy techniques described, below, e.g., to evaluate the normal and/or engineered IGFBP-3 MUTANT-expressing cells prior to their introduction into the patient. Such antibodies may additionally be used as a method for the modulation of normal or abnormal IGFBP-3 MUTANT activity. Thus, such antibodies may, therefore, be utilized as part of cancer treatment methods.

For the production of antibodies, various host animals may be immunized by injection with the IGFBP-3 MUTANT, an IGFBP-3 MUTANT peptide, truncated IGFBP-3 MUTANT polypeptides (IGFBP-3 mutant in which one or more domains has been deleted), functional equivalents of the IGFBP-3 MUTANT or mutants of the IGFBP-3 MUTANT. Such host animals may include but are not limited to rabbits, mice, hamsters and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyani, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals. Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (*Nature* 256:495-497, 1975; and U.S. Pat. No. 4,376,110), the human B-cell hybridoma technique (Kosbor et al., *Immunology Today* 4:72, 1983; Cole et al., *Proc. Natl. Acad. Sci. USA* 80:2026-2030, 1983), and the EBV-hybridoma technique (Cole et al., *Monoclonal Antibodies And Cancer Therapy*, Alan R. Liss, Inc., pp. 77-96, 1985). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci. USA*, 81:6851-6855, 1984; Neuberger et al., *Nature*, 312: 604-608, 1984; Takeda et al., *Nature*, 314: 452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (humanized).

Alternatively, techniques described for the production of single-chain antibodies (U.S. Pat. No. 4,946,778; Bird, *Science* 242:423-426, 1988; Huston et al., *Proc. Natl. Acad. Sci. USA* 85:5879-5883, 1988; and Ward et al., *Nature* 334:544-546, 1989) can be adapted to produce single-chain antibodies against IGFBP-3 MUTANT gene products. Single-chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, that can be produced by pepsin digestion of the antibody molecule; and the Fab fragments, that can be generated by reducing the disulfide bridges of the F(ab')$_2$ fragments. Alternatively, Fab expression libraries may be constructed (Huse et al., *Science,* 246:1275-1281, 1989) to allow rapid and easy identification of monoclonal Fab fragments with the desired specificity.

Antibodies to the IGFBP-3 MUTANT can, in turn, be utilized to generate anti-idiotype antibodies that "mimic" the IGFBP-3 MUTANT, using techniques well known to those skilled in the art. (Greenspan & Bona, *FASEB J* 7 (5):437-444, 1993; and Nissinoff, *J. Immunol.* 147:2429-2438, 1991). For example antibodies that bind to the IGFBP-3 MUTANT and competitively inhibit the binding of IGFBP-3 to the P4.33 can be used to generate anti-idiotypes that "mimic" the IGFBP-3 MUTANT and, therefore, bind and neutralize IGFBP-3. Such neutralizing anti-idiotypes or Fab fragments of such anti-idiotypes can be used in cancer therapeutic regimens to neutralize the native ligand.

Alternatively, antibodies can be generated against IGFBP-3 MUTANT that can act as agonists of IGFBP-3 MUTANT. Such antibodies will bind to the IGFBP-3 MUTANT and activate the signal transducing activity of the IGFBP-3: P4.33 complex. In addition, antibodies that act as antagonist of IGFBP-3 MUTANT activity, i.e., inhibit the activation or signaling by P4.33, may be used to treat cancer.

Gene Therapy Approaches to Controlling IGFBP-3 Mutant Expression for Treating Cancer The expression of IGFBP-3 mutants can be controlled in vivo (e.g., at the transcriptional or translational level) using gene therapy approaches to regulate IGFBP-3 mutant activity and treat cancer. Certain approaches are described below.

Gene Replacement Therapy. With respect to modulating (competing with) the level of normal IGFBP-3 gene expression and/or P4.33 gene product activity, IGFBP-3 mutant nucleic acid sequences can be utilized for the treatment of cancer, including lung, cervical, breast, colon or prostate carcinoma. A IGFBP-3 mutant gene product may be inserted into the appropriate cells within a patient or animal subject, using vectors that include, but are not limited to adenovirus, adeno-associated virus, retrovirus and herpes virus vectors, in addition to other particles that introduce DNA into cells, such as liposomes.

Because the P4.33 gene is expressed in the brain, possibly including the cortex, thalamus, brain stem and spinal cord and hypothalamus, such gene replacement therapy techniques should be capable of delivering IGFBP-3 mutant gene sequences to these cell types within patients. Thus, the techniques for delivery of the IGFBP-3 mutant gene sequences should be designed to readily cross the blood-brain barrier, that are well known to those of skill in the art (PCT WO89/10134, which is incorporated herein by reference in its entirety), or, alternatively, should involve direct administration of such IGFBP-3 mutant gene sequences to the site of the cells in which the IGFBP-3 mutant gene sequences are to be expressed.

Additional methods which may be utilized to increase the overall level of IGFBP-3 mutant gene expression and/or IGFBP-3 mutant activity include the introduction of appropriate IGFBP-3 mutant-expressing cells, preferably autologous cells, into a patient at positions and in numbers which are sufficient to ameliorate the progression of cancer. Such cells may be either recombinant or non-recombinant. Among the cells which can be administered to increase the overall level of IGFBP-3 mutant gene expression in a patient are normal cells, or e.g., hypothalamus cells, that express the IGFBP-3 mutant gene. The cells can be administered at the anatomical site in the brain, or as part of a tissue graft located at a different site in the body. Such cell-based gene therapy techniques are well known to those skilled in the art (Anderson et al., U.S. Pat. No. 5,399,349; Mulligan & Wilson, U.S. Pat. No. 5,460,959). Finally, compounds, identified in the assays described above, that stimulate or enhance the signal transduced by activated P4.33, e.g., by activating downstream signaling proteins in the P4.33 signal transduction pathway, can be used to treat cancer. The formulation and mode of administration will depend upon the physico-chemical properties of the compound. The administration should include known techniques that allow for a crossing of the blood-brain barrier.

Vectors can be plasmid, viral, or others known in the art, used for replication and expression in mammalian cells. Expression can be by any promoter known in the art to act in mammalian, preferably human cells. Such promoters can be inducible or constitutive. Such promoters include but are not limited to: the SV40 early promoter region (Benoist and Chambon, *Nature* 290:304-310, 1981), the promoter contained in the 3' long terminal repeat of Rous sarcoma virus (Yamamoto et al., *Cell* 22:787-797, 1980), the herpes thymidine kinase promoter (Wagner et al., *Proc. Natl. Acad. Sci. USA* 78:1441-1445, 1981), the regulatory sequences of the metallothionein gene (Brinster et al., *Nature* 296:39-42, 1982). Any type of plasmid, cosmid, YAC or viral vector can be used to prepare the recombinant DNA construct that can be introduced directly into the tissue site; e.g., the tumor or other tissues. Alternatively, viral vectors can be used which selectively infect the desired tissue; (e.g., for brain, herpesvirus vectors may be used), in which case administration may be accomplished by another route (e.g., systemically).

Screening Assays for Drugs Useful in Cancer Treatment

At least three different assay systems can be designed and used to identify compounds or compositions that modulate IGFBP-3 mutant activity and therefore, modulate cancer. The systems described below may be formulated into kits. To this end, the IGFBP-3 mutant or cells expressing the IGFBP-3 mutant can be packaged in a variety of containers, e.g., vials, tubes, microtitre well plates, bottles, and the like. Other reagents can be included in separate containers and provided with the kit; e.g., positive controls samples, negative control samples, IGFBP-3 mutant peptides, buffers, cell culture media, antibodies, etc.

Cell-Based Assays. In accordance with the invention, a cell-based assay system can be used to screen for compounds that modulate the activity of the IGFBP-3R to identify compounds for the treatment of cancer. To this end, cells that endogenously express IGFBP-3 Receptor and/or IGFBP-3 mutants can be used to screen for compounds. Alternatively, cell lines, such as 293 cells, COS cells, CHO cells, MCF-7 cells, Hs578T cells, fibroblasts, and the like, genetically engineered to express IGFBP-3 receptor and/or IGFBP-3 mutants, can be used for screening purposes. Preferably, host cells genetically engineered to express a functional IGFBP-3 receptor that either responds to activation by IGFBP-3 or IGFBP-3 mutant peptides, can be used as an endpoint in the assay; e.g., as measured by a chemical, physiological, biological, or phenotypic change, induction of a host cell gene or a reporter gene, change in cAMP levels, adenylyl cyclase activity, host cell G-protein activity, extracellular acidification rate, host cell kinase activity, proliferation, differentiation, etc.

To be useful in screening assays, the host cells expressing functional IGFBP-3 receptor and/or IGFBP-3 mutant should give a significant P4.33-based response to, preferably greater than 5-fold induction over background. Host cells should preferably possess a number of characteristics, depending on the readout, to maximize the P4.33-based inductive response. For example, in the case of some art-recognized receptors, detecting a strong induction of a CRE reporter gene: (a) a low natural level of cAMP, (b) a high level of adenylyl cyclase, (c) a high level of protein kinase A, (d) a low level of phosphodiesterases, and (e) a high level of cAMP response element binding protein would be advantageous. To increase P4.33-based responses, host cells could be engineered to express a greater amount of favorable factors or a lesser amount of unfavorable factors. In addition, alternative pathways for induction of the CRE reporter could be eliminated to reduce basal levels.

In utilizing such cell systems, the cells expressing the P4.33 and/or IGFBP-3 mutant are exposed to a test compound or controls. After exposure, the cells can be assayed to measure the expression and/or activity of components of the signal transduction pathway of P4.33 and/or IGFBP-3, or the activity of the signal transduction pathway itself can be assayed. For example, after exposure, cell lysates can be assayed for induction of cAMP, or modulation of Ras, PKA, RAP1, B-Raf, Mek, or MAPK, type II collagen and/or proteoglycan. In screening for compounds that may act as agonists of IGFBP-3 mutant/P4.33, it may be advantageous to use cell lines that express little or no IGFBP-3 to test for activation of signal transduction by the test compound as compared to controls. In screening for compounds that may act as antagonists of IGFBP-3 mutant/P4.33, it may be advantageous to overexpress IGFBP-3 to test for inhibition of signal transduction by the test compound as compared to controls.

P4.33 may undergo IGFBP-3-mediated intracellular nuclear transport. In another embodiment of the invention, test compounds are selected based on their ability to regulate nuclear translocation of P4.33 and/or IGFBP-3 mutant or IGFBP-3 mutant:P4.33 complex.

Non-Cell-Based Assays. In addition to cell-based assays, non-cell-based assay systems may be used to identify compounds that interact with, e.g., bind to IGFBP-3 mutant, P4.33 or to IGFBP-3 mutant:P4.33 complex. Such compounds may act as agonists or antagonists of IGFBP-3 mutant/P4.33 or IGFBP-3 activity and may be used in the treatment of cancer. Soluble IGFBP-3 receptor may be recombinantly expressed and utilized in non-cell based assays to identify compounds that bind to IGFBP-3 mutant or to IGFBP-3 mutant:P4.33 complex. Recombinantly expressed IGFBP-3 receptor, polypeptides or fusion proteins can be used in the non-cell based screening assays, with or without IGFBP-3 polypeptides or fusion proteins. Alternatively, peptides corresponding to one or more IGFBP-3 mutant domains, or fusion proteins containing one or more of the IGFBP-3 mutant domains can be used in non-cell based assay systems to identify compounds that bind to IGFBP-3 mutant or to IGFBP-3 mutant:P4.33 complex. Such compounds may be useful to modulate the signal transduction pathway of P4.33 or IGFBP-3. In non-cell based assays the recombinantly expressed IGFBP-3 mutant polypeptide or fusion protein, or IGFBP-3 mutant:P4.33 complex, or P4.33 may be attached to a solid substrate such as a test tube, microtitre well or a column, by means well known to those in the art. The test compounds are then assayed for their ability to bind to the IGFBP-3 mutant, P4.33 or IGFBP-3 mutant:P4.33 complex.

In one aspect of the invention the screens may be designed to identify compounds that mimic the interaction between P4.33 and P4.33 ligands such as IGFBP-3 mutant. In such screens, the test compounds are labeled, and can be assayed for their ability to bind to P4.33 or IGFBP-3 mutant. In another aspect of the invention the screens may be designed to identify compounds that antagonize the interaction between P4.33 and P4.33 ligands such as IGFBP-3 mutant. In such screens, the P4.33 ligands (i.e., IGFBP-3 mutant) are labeled and test compounds can be assayed for their ability to antagonize the binding of labeled ligand to P4.33.

Compounds that can be Screened in Accordance with the Invention

The assays described above can identify compounds that affect P4.33 or IGFBP-3 mutant:P4.33 complex activity. For example, compounds that affect P4.33 or IGFBP-3 IGFBP-3 mutant:P4.33 complex activity include but are not limited to compounds that bind to the P4.33, inhibiting or not inhibiting binding of the natural ligand (IGFBP-3), and either activate signal transduction (agonists) or block activation (antagonists), and compounds that bind to the natural ligand of P4.33 and neutralize or enhance ligand activity. Compounds that affect P4.33 gene activity (by affecting P4.33 gene expression, including molecules, e.g., proteins or small organic molecules, that affect transcription or interfere with splicing events so that expression of the full-length or the truncated form of P4.33 can be modulated) can also be identified on the screens of the invention. However, it should be noted that the assays described can also identify compounds that modulate P4.33 signal transduction (e.g., compounds which affect downstream signaling events, such as inhibitors or enhancers of G protein activities, or of, e.g., Ras, PKA, RAP1, B-Raf, Mek, or MAPK, which may participate in transducing the signal activated by IGFBP-3 binding to the P4.33). The identification and use of such compounds that affect signaling events downstream of P4.33 and thus modulate effects of P4.33 on the cancer progression are within the scope of the invention.

The compounds which may be screened in accordance with the invention include, but are not limited to peptides, antibodies and fragments thereof, and other organic compounds (e.g., peptidomimetics) that bind to P4.33 or IGFBP-3 mutant:P4.33 complex and either mimic the activity triggered by IGFBP-3 (i.e., agonists) or inhibit the activity triggered by IGFBP-3 (i.e., antagonists); as well as IGFBP-3 mutant peptides, antibodies or fragments thereof, and other organic compounds that include that compete with IGFBP-3. Compounds may include, but are not limited to, peptides such as, for example, soluble peptides, including but not limited to members of random peptide libraries; (Lam et al., *Nature* 354:82-84, 1991; Houghten et al., *Nature* 354:84-86, 1991), and combinatorial chemistry-derived molecular library made of D- and/or L-configuration amino acids, phosphopeptides (including, but not limited to, members of random or partially degenerate, directed phosphopeptide libraries; e.g., Songyang et al., *Cell* 72: 67-778, 1993), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules. Other compounds which can be screened in accordance with the invention include, but are not limited to, small organic molecules that are able to cross the blood-brain barrier, gain entry into an appropriate cell and P4.33 signal transduction pathway (e.g., by interacting with the regulatory region or transcription factors involved in gene expression); or such compounds that affect the activity of P4.33 or the activity of some other intracellular factor involved in the P4.33 signal transduction pathway, such as, e.g., IGFBP-3, Ras, PKA, RAP1, B-Raf, Mek, or MAPK.

Delivery of Soluble IGFBP-3 Mutant Polypeptides

Genetically engineered cells that express soluble IGFBP-3 mutant domains, or IGFBP-3 mutant fusion proteins thereof, e.g., fusion Ig molecules or IGFBP-3 mutant-$t^{HA}$, can be administered in vivo where they may function as competitors. Such soluble IGFBP-3 mutant polypeptides and fusion proteins, when expressed at appropriate concentrations, could modulate endogenous IGFBP-3 activity, or compete with the native ligand for P4.33 (i.e., IGFBP-3) and thus act as modulators of P4.33 activity for cancer treatment purposes.

Pharmaceutical Formulations and Methods of Treating Cancer

The invention encompasses methods and compositions for treating cancer. Because enhancement of P4.33 gene product function in the presence of IGFBP-3 results, in growth inhibition and cell death (apoptosis) enhancement of P4.33 activity in such cells would facilitate progress in treating cancers such as, e.g., lung, cervical, breast, colon or prostate carcinomas. Alternatively, progression of certain cancers may be facilitated by higher than normal levels of P4.33 gene expression, and/or P4.33 gene activity. In these cases, down regulating activity of the P4.33 pathway (e.g., by targeting downstream signaling events) may be useful in treating cancer. Different approaches are discussed. Agonists of P4.33 can be used to induce apoptosis in certain cancers such as, e.g., lung, cervical, breast, colon or prostate carcinomas. Antagonists of P4.33 activity may also be useful in these or other cancer types. It is not necessary that the compound demonstrate absolute specificity for the P4.33. For example, compounds that agonize both P4.33, and other unknown IGFBP-3 interaction molecules, could be used. Such compounds could be administered so that delivery to breast tissue, the prostate, or elsewhere, is optimized to achieve cancer treatment, and potential side effects may well be tolerated. Compounds that do not demonstrate a specificity for P4.33 can be administered in conjunction with another therapy or drug to control the side-effects that may result from modulating other molecules (e.g., other IGFBP-BPs); however, compounds which demonstrate a preference or selectivity for IGFBP-3 or IGFBP-3:P4.33 complex are preferred.

Dose Determinations. Toxicity and therapeutic efficacy of such compounds can be determined by standard pharmaceutical and toxicologic procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Formulations and Use. Pharmaceutical compositions for use in accordance with the present invention may be formulated in a conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulary agents such as suspending, stabilizing and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (e.g., as an emulsion in an acceptable oil) or ion-exchange resins, or as sparingly soluble derivatives, for example, as a sparingly soluble salt.

The compositions may, if desired, be presented in a pack or dispenser device that may contain one or more unit dosage forms containing the active ingredient. The pack may, for example, comprise metal or plastic foil, such as a blister pack. The pack or dispenser device may be accompanied by instructions for administration.

MATERIALS AND METHODS

Materials $[^{125}I]$-IGF-I and -II were provided by Diagnostic System Laboratories, Inc. (Webster, Tex.). IGF-I and -II were purchased from Austral Biologicals (Santa Clara, Calif.). Reagents for SDS-PAGE were purchased from Bio-Rad Laboratories, Inc. (Hercules, Calif.). The BIAcore X instrument, sensor chip CM5 (research grade), HBS-EP buffer (0.01 M HEPES, 0.15 M NaCl, 3 mM EDTA, and 0.005% Surfactant P20, pH 7.4), and the amine coupling kit containing N-hydroxysuccinimide (NHS), N-ethyl-N'-(3-diethylaminopropyl)carbodiimide (EDC), and ethanolamine hydrochloride were purchased from BIAcore AB (Uppsala, Sweden). For use in the BIAcore analysis, rhIGF-I was a gift from Genentech (South San Francisco, Calif., USA), and rhIGF-II was a gift from Pharmacia (Uppsala, Sweden).

Cell Culture

Cos-7 cells were obtained from American Type Culture Collection (Rockville, Md.) and grown in DMEM with 10% FCS at 37 C in 5% CO2. NIH-3T3 cells were a gift from Dr. C. T. Roberts, Jr. (Department of Pediatrics, Oregon Health Sciences University) and were grown in DMEM with 10% FCS and 500 µg/ml G418 at 37 C in 5% CO2. All tissue culture media and components were purchased from Life Technologies, Inc. (Grand Island, N.Y.), except FCS from HyClone Laboratories, Inc. (Logan, Utah).

Generation, Purification, and Quantitation of Recombinant IGFBP-3 Deletion Fragments, Wild-type, and Mutants The CDNAs of $^{(1-46)}$, $^{(1-75)}$, $^{(1-80)}$, and $^{(187)}$IGFBP-3 FLAG-epitope tagged fragments were generated by polymerase chain reaction amplification from the human IGFBP-3 cDNA and a C-terminal FLAG epitope sequence (DYKDDDDK). After sequencing sense and anti-sense strands, the fragments were then subcloned into pGEX4T-1 (Amersham Pharmacia Biotech, Piscataway, N.J.) and transformed into BL21DE3 E. coli cells, cultured overnight in LB-ampicillin, and induced with 2 mM IPTG. Cell lysates were then harvested and analyzed by SDS-PAGE stained with Coomassie blue, and also by Western immunoblot with M2 anti-FLAG antibody (Eastman Kodak Co., Rochester N.Y.).

The preparation of expression vector pBSSK:IGFBP-3, containing a full-length human IGFBP-3 cDNA with a C-terminal FLAG epitope sequence (DYKDDDDK), by PCR amplification was as described previously (Vorwerk et al., *J. Clin. Endocrinol Metab.* 82:2368-70, 1997). Single-stranded phagemid-DNA was generated from pBSSK:IG-FBP-3$^{FLAG}$, and mutations were introduced using synthetic degenerate oligonucleotides as substrates for antisense DNA synthesis. The following complementary oligonucleotide (SEQ ID NO:1) was used to mutate I56 to V56 or G56 with an Ac1 I site: agc gag ggc cag ccg tgc ggc mkc tac acc gaa cgt tgt ggc tce ggc ctt cgc (m=a or c; k=t or g). The following complementary oligonucleotide (SEQ ID NO:2) was used to mutate L80 and L81 to V80 or G80 and/or V81 or G81 without a Pst I site: gag gcg cga ccg ctg caa gcg skg gac ggc cgc ggg ctc tgc gt (s=c or g; k=t or g). Sense and anti-sense strands were sequenced, and preps were subcloned into pCMV6 for transient transfections of Cos-7 cells, into pGEX4T-1 for generation of *E. coli* GST-fusion cell lysates as described above, and into pFASTBAC1 (Life Technologies, Inc., Grand Island, N.Y.) for Baculovirus-generated proteins as described below. The full-length IGFBP-3 triple G mutant was constructed by subcloning a G80G81 fragment into the pCMV6:G56 mutant with Bam HI and Bst API.

pFASTBAC1 preps were transformed into DH10Bac *E. coil* cells. The amplified DNA was transfected into Sf9 insect cells (ATCC, Rockville, Md.). HIGH-5 insect cells (Invitrogen, Carlsbad, Calif.) were infected with P2 virus. The media were harvested on the 3$^{rd}$ day and incubated with an anti-M2 antibody affinity column overnight at 4 C. The FLAG-tagged protein was then eluted by using FLAG peptide as previously described earlier (Oh et al., *J Biol. Chem.* 271:30322-5, 1996). Eluted fractions were analyzed on 12% SDS-PAGE under non-reducing conditions, followed by staining with Coomassie blue. Fractions were pooled and quantitated by two methods: (a) comparison with known quantities of Baculovirus IGFBP-3 by silver staining (Bio-Rad Laboratories, Inc., Hercules, Calif.); and (b) IGFBP-3 IRMA analysis (Diagnostic Systems Laboratories, Inc., Webster, Tex.).

Transient Transfections of Cos-7 Cells

Cells were plated in 6-well plates and grown to 50-70% confluence and transfected with a 1:2 ratio of cDNA and Mirrus Transit LT-1 (PanVera, Madison, Wis.). Medium was changed to serum-free after 16 h, then collected 48 h later, and cellular debris was removed by centrifugation.

Western Ligand Blot Analysis

Samples of *E. coli*-generated GST-fusion cell lysates, purified Baculovirus-expressed proteins, or conditioned media at the concentrations indicated in the figure legends were mixed with Laemmli sample buffer without a reducing agent and heated at 95° C. for 5 minutes, then electrophoresed on a 12% SDS gel, and electroblotted onto nitrocellulose. For dot blots, 2.5 µl of sample were dotted directly onto the nitrocellulose membrane. Membranes were then blocked for 1 h at 21° C. in 1% BSA/TBS-T (Tris-buffered saline-Tween-20, 0.1%), then incubated at 4° C. overnight with 1×10$^6$ cpm of $[^{125}I]$-IGF-I, [125I]-IGF-II, or a mixture of the two. The membranes were then washed, dried, and exposed to Biomax MS film (Eastman Kodak Co., Rochester, N.Y.). The same membranes were then probed with antibodies as described below. Bands were quantified using an image analyzer (GS-700) equipped with MultiAnalyst version 1.0.2 Software (Bio-Rad Laboratories, Inc., Hercules, Calif.).

Western Immunoblot Analysis

Samples of *E. coli*-generated GST-fusion cell lysates, purified Baculovirus-expressed proteins, whole cell lysates, or conditioned media at the concentrations indicated in the figure legends were mixed with Laemmli sample buffer with or without a reducing agent and heated at 95° C. for 5 minutes, then subjected to SDS-PAGE (8% or 12% gels), and electroblotted onto nitrocellulose membranes. For dot blots, 2.5 µl of sample were dotted directly onto the nitrocellulose membrane. The membranes were then blocked for 1 h at 21° C. in 4% milk/TBS-T, followed by an overnight incubation at 4° C. with anti-IGFBP-3 monoclonal antibody (Diagnostic Systems Laboratories, Inc., Webster, Tex.), anti-GST polyclonal antibody (Amersham Pharmacia Biotech, Piscataway, N.J.), anti-PY20 monoclonal antibody (Santa Cruz Biotech, Santa Cruz, Calif.), or anti-IRS-1 polyclonal antibody (Upstate, Lake Placid, N.Y.), all at 1:3000 dilutions. Membranes were washed with TBS-T and incubated for 1 h at 21° C. with a 1:3000 dilution of horseradish peroxidase-linked antirabbit or antimouse IgG secondary antibodies (Amersham Pharmacia Biotech, Piscataway, N.J.). Proteins were detected by enhanced chemiluminescence reagents, according to the manufacturer's protocol (NEN Life Science Products, Boston, Mass.).

Affinity Cross-linking

E. coli generate GST-fusion cell lysates of full-length IGFBP-3 or mutants were incubated with 50,000 cpm [$^{125}$I]-IGF-I in the presence or absence of unlabeled IGF-I (100 nM) overnight at 4° C. and then crosslinked with 0.5 mM disuccinimidyl suberate (DSS) for 15 min at 4° C. The samples were quenched with 100 mM Tris pH 7.4 and were then subjected to 12% SDS-PAGE and autoradiography on Biomax MS film (Eastman Kodak Co., Rochester, N.Y.).

Solution Binding Assay

Increasing amounts (0-100 ng/ml) of purified Baculovirus IGFBP-3 or mutant proteins in duplicate were incubated in 500 µl of buffer (50 mM Tris pH 7.4+0.5% BSA) with 10,000 cpm of [$^{125}$I]-IGF-I at 4° C. overnight. One ml of activated charcoal solution (0.5% activated charcoal, 0.2 mg/ml protamine sulfate, and 1% BSA in PBS) was added for 10 min and then centrifuged for 10 min at 4000 rpm at 4° C. to separate bound and free IGF-I. A gamma counter was used to measure the radioactivity of the supernatants.

BIAcore Analysis

Equal volumes of NHS and EDC were mixed and 35 µl of the mixture was injected over the surface of the sensor chip to activate the carboxymethylated dextran. Eighty-three µl of purified Baculovirus-generated wild-type or mutant IGFBP-3 solution (15 µg/ml in 10 mM NaAc pH 4.5) was injected over the activated surface, followed by 35 µl of ethanolamine to deactivate remaining active carboxyl groups. The immobilization procedure was carried out at 25° C. and at a constant flow rate of 5 µl/min. The first of the two flow cells of each chip was used as an in-line blank reference cell. The carboxymethylated dextran in the reference cell was activated and deactivated as described above, but without any ligand bound. All experiments were carried out at 25° C. and at a constant flow rate of 10 µl/min HBS-EP buffer. Thirty-five µl of the analyte (IGF-I or IGF-II) diluted in HBS-EP buffer was injected over the immobilized wild-type or mutant IGFBP-3, followed by a 5 min period where buffer was passed over the surface. Six concentrations of IGF-I and IGF-II were passed over each chip, 3.13 nM, 6.25 nM, 12.5 nM, 25 nM, 50 nM, and 100 nM. All kinetic assays were followed by an injection of 15 µl 0.1 M HCl in order to dissociate the remaining ligand from the binding protein. The experiment was performed a total of three separate times. BIAevaluation 3.0 software and Sigma Stat were used for data analysis, and a 1:1 mass transfer curve-fitting model was used in the evaluation.

IGF-I-Induced IGFIR Autophosphorylation Assay

Confluent monolayers of NIH-3T3-IGFIR cells were incubated in serum-free medium overnight. Purified Baculovirus IGFBP-3 and mutant proteins (250 ng) were incubated with IGF-I (100 ng) in 1 ml of DMEM+0.05% BSA for 30 min at 21° C. and then added to the cells for 10 min. The reaction was quenched with solubilization buffer (50 mM Tris pH 7.5, 2.5 mg/ml sodium deoxycholate, 150 mM sodium chloride, 1 mM sodium orthovanadate, 20 mM sodium fluoride, 1% NP40). Samples were normalized for protein concentration using a DC protein assay (Bio-Rad Laboratories Inc., Hercules, Calif.), and were separated on 8% SDS-PAGE under reducing conditions. Anti-PY20 or anti-IRS-1 antibodies were used for Western immunoblot.

EXAMPLE 1

The Hydrophobic Pocket of IGFBP-5

Figure 2:
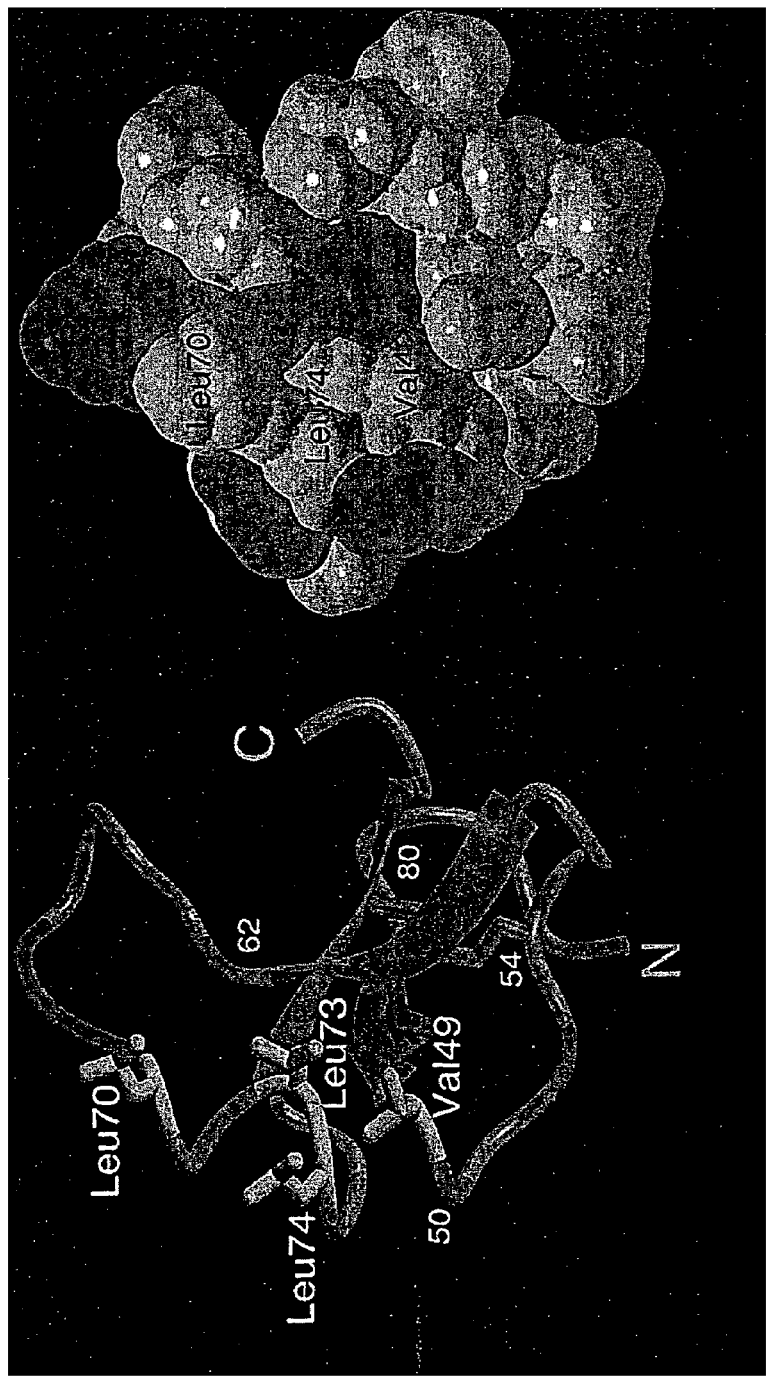
FIG. 2 summarizes NMR-based data from Kalus et al. (EMBO J. 17:6558-6572, 1998), illustrating that IGFBP-5 has an N-terminal hydrophobic patch. The hydrophobic patch amino acids are so-identified.
Figure 4:
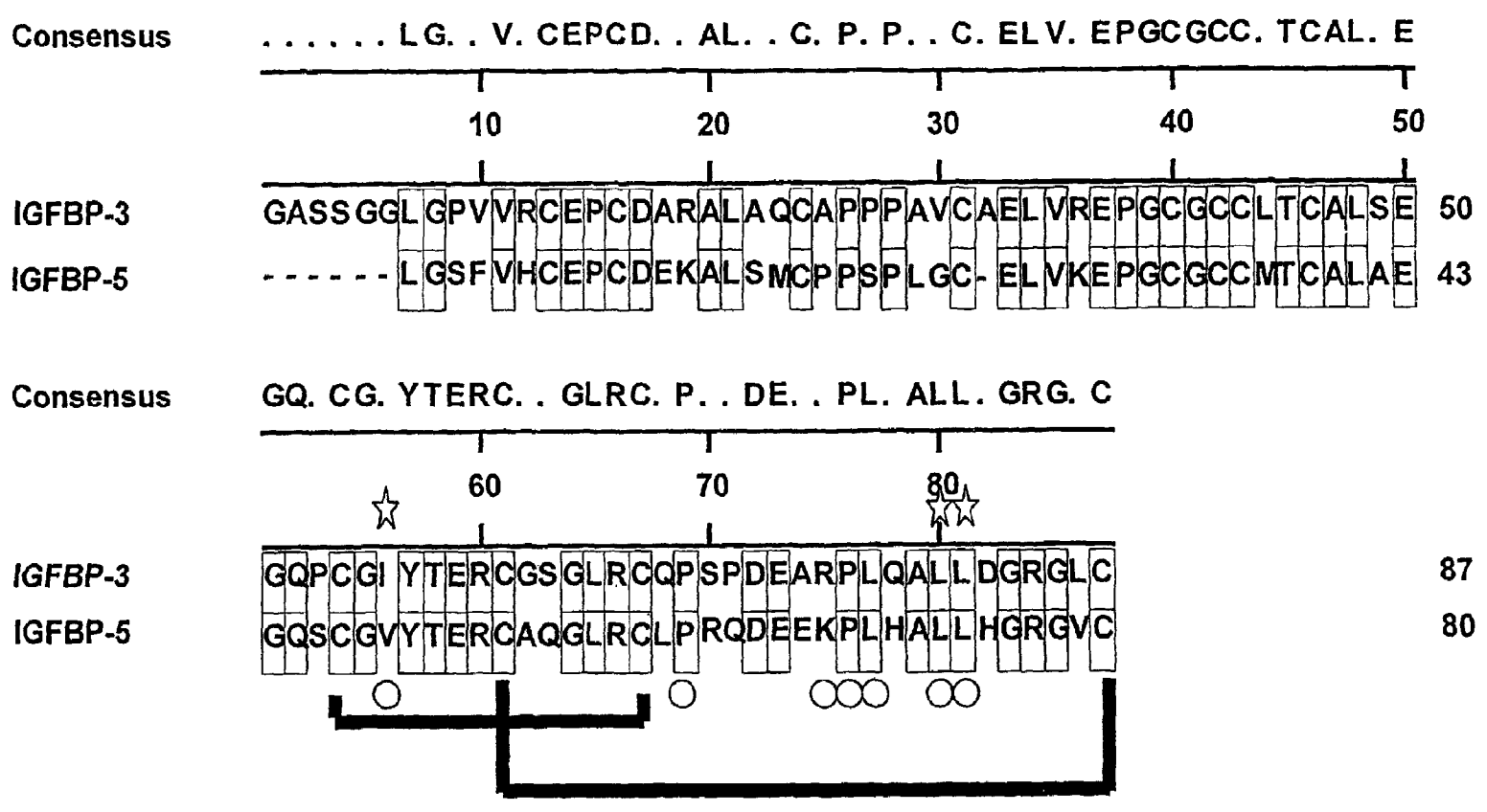

The hydrophobic patch region of IGFBP-5 contains amino acid residues that are important for binding IGF. FIG. 2 shows data from Kalus et al. (EMBO J. 17:6558-6572, 1998) that illustrates, based on NMR studies, that IGFBP-5 has an N-terminal hydrophobic patch. The Hydrophobic patch amino acids are identified in the figure. Additionally, FIG. 3 shows data from Imai et al. (*J. Biol. Chem.* 275: 18188-18194, 2000) illustrating that mutations involving 5 amino acids in IGFBP-3 (as shown in the lower portion of FIG. 3), abolishing IGF binding, as predicted by Kalus et al., based on the consensus hdrophobic region in BP-5. FIG. 4 shows an amino acid sequence comparison of IGFBP-3 and IGFBP-5. The "consensus," or identical amino acids between these two proteins are framed in boxes. Circles below certain amino acids identify those amino acids predicted to be important for IGF interaction based on the NMR studies of IGFBP-5 (Kalus et al.). The stars above particular amino acid positions, identify 3 amino acids in IGFBP-3 that were mutated according to the present invention.

EXAMPLE 2

Comparison of Deltion Mutants of IGFBP-3 in Binding IGF Indicated that IGF Binding Required Amino Acids 1-87 of IGFBP-3

Expression and Analysis of *E. coli*-Generated GST-Fusion IGFBP-3 Deletion Fragments. Fragments of the N-terminus of IGFBP-3 were constructed by PCR amplification and expressed as GST-fusion cell lysates in *E. coli*. Amplification of the peptides was confirmed by SDS-PAGE and Coomassie staining. Binding to [$^{125}$I]-IGF-I was screened by dot blot analysis (FIG. 1, upper panel) as described under "Materials and Methods."

Specfically, FIG. 1 shows dot blot ligand blot and immuno blot analyses of the [$^{125}$I]-IGF-I binding affinity of various IGFBP-3 N-terminal deletion fragments. The upper panel shows a dot ligand blot of IGFBP-3 fragments corresponding to amino acids 1-46, 1-75, 1-80, and 1-87 that were generated by polymerase chain reaction, and expressed and produced in *E. coli* as GST-fusion proteins. Lane 1, $^{(146)}$IGFBP-3; lane 2, $^{(1-75)}$IGFBP-3; lane 3, $^{(1-80)}$IGFBP-3; lane 4, $^{(1-87)}$IGFBP-3; lane 5, full-length IGFBP-3; lane 6, pGEX4T-1 vector alone. The binding of these IGFBP-3

"deletion" fragments to [$^{125}$I]-IGF-I is shown, along with wild-type IGFBP-3 binding, and control vector (pGEX4T-1) to [$^{125}$I]-IGF-I. For each protein sample, the protein extract was directly pipetted onto nitrocellulose paper, incubated in 1% BSA with [$^{125}$I]-IGF-I, and then exposed to film. A dot immunoblot (lower panel), using an antibody to GST, established that equal amounts of protein were used among the various samples.

Strong [$^{125}$I]-IGF-I binding was detected for both full-length IGFBP-3, and for $^{(1-87)}$IGFBP-3 GST-fusion fragment. No binding was detected for the smaller fragments ($^{1-80,\ 1-75,}$ and $^{1-46}$).

EXAMPLE 3

Nonconserved Amino Acid Substitutions at Amino Acids I56, L80 and L81 of Full-length IGFBP-3 Decreased or Abolished IGF Binding Screening Binding Studies of Bacterially-Expressed IGFBP-3 Mutant Proteins. The studies with deletion fragments indicated that N-terminal residues were crucial to the binding of IGF. Therefore, three of the amino acids (I56, L80, and L81) in this region were mutated in various combinations, either to a conserved residue, valine, or to a non-conserved residue, glycine (FIGS. 4 and 5). Various conservative and nonconservative single, double and triple mutants were made.

Initial [$^{125}$I]-IGF-I ligand binding studies were by dot blot analysis (FIG. 6, upper panel) of E. coli GST-fusion proteins as described above. Briefly, 2.5 µl of cell lysate was dotted directly onto nitrocellulose membrane and incubated overnight with 1×10$^6$ cpm $^{125}$I-IGF-I and -II overnight, and corresponding immunoblot with anti-GST antibody. Lane 1, IGFBP-3; lane 2, pGEX4T-1 vector; lane 3, G56 mutant; lane 4, V56 mutant; lane 5, G80G81 mutant; lane 6, V80V81 mutant.

Figure 6:
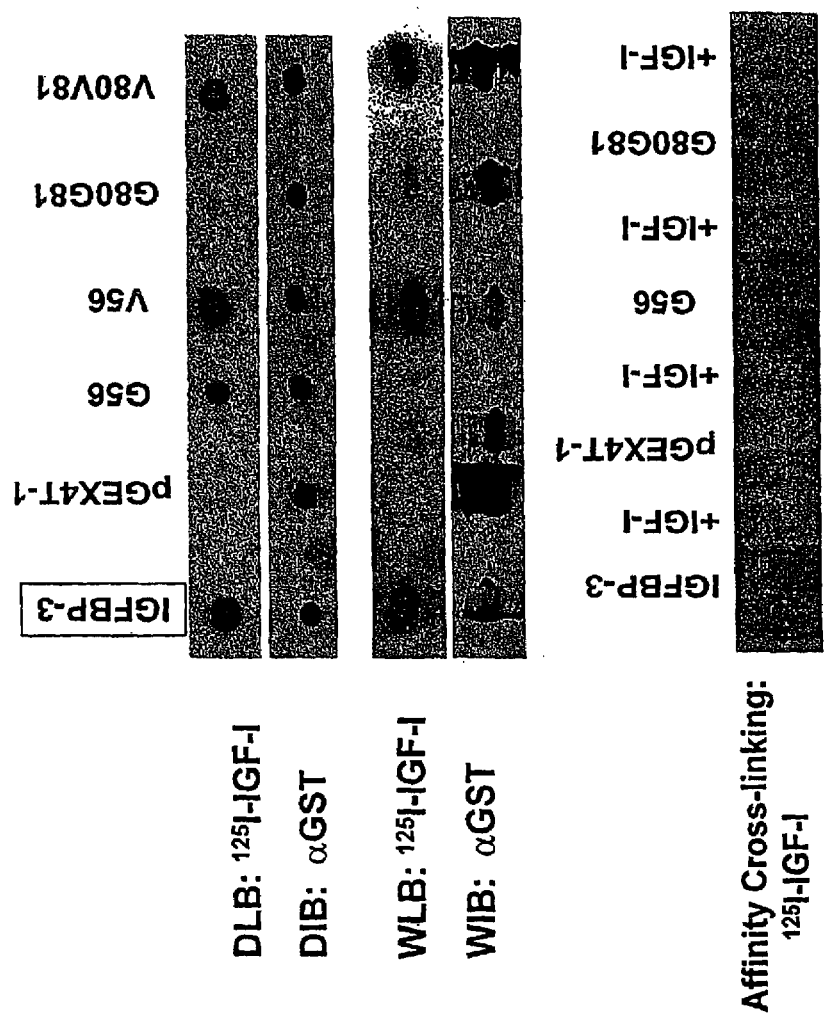
FIG. 6 shows dot ligand blot and Western ligand blot analysis of the $[^{125}I]$-IGF-I binding affinity of bacterially-expressed IGFBP-3 mutants (as *E. coli*-generated GST-fusion proteins) of the present invention. There was no significant decrease in binding with conserved mutations to Valine ("V56" and "V80V81" double mutant lanes), some decrease in binding with the nonconserved G56 mutant alone ("G56" lane), and a marked reduction with nonconserved G80G81 double mutant ("G80G81" lane) (upper panels). An affinity cross-linking experiment (lower panel) confirmed that binding to $[^{125}I]$-IGF-I was reduced with the nonconserved G56 mutation ("G56") and abolished with nonconserved G80G81 double mutant ("G80G81").

These data were confirmed by Western ligand blots on 12% SDS-PAGE (FIG. 6, middle panel). Briefly, 20 µl of protein was applied per lane on a 12% SDS-PAGE gel under nonreducing conditions, incubated overnight with 1×10$^6$ cpm $^{125}$I-IGF-I and -II; the same membrane was probed with anti-GST antibody for comparison of cell lysate concentrations. Lanes were as described in for the upper panel of FIG. 6.

Both methods showed minimal change in [$^{125}$I]-IGF-I binding when the large, nonpolar, hydrophobic residue, valine, was substituted for I56 or for L80L81 ("V56" and "V80V81" double mutant lanes). However, a clear reduction in [$^{125}$I]-IGF-I binding was observed with substitution of I56 or L80L81 by glycine ("G56" and "G80G81" lanes, respectively), a small, polar amino acid (non-conservative mutations). That equal amounts of protein were applied in each case was confirmed with immunoblots using anti-GST antibody.

As predicted, the valine mutants showed relatively little change in IGF affinity, and they were not further tested. The glycine mutants, however, were also tested in an affinity cross-linking study, in which they were incubated with [$^{125}$I]-IGF-I and cross-linked prior to gel electrophoresis FIG. 6, lower panel). Briefly, affinity cross-linking was performed with 20 microliters of protein with 50,000 cpm $^{125}$I-IGF-I after overnight incubation at 4° C., run on 12% SDS-PAGE, and exposed to film. Lanes 1 & 2, IGFBP-3 and lane 3, IGFBP-3 with competition by unlabeled IGF-I; lanes 4 & 5, pGEX4T-1 vector alone and lane 6, pGEX4T-1 with unlabeled IGF-I; lanes 7 & 8, G56 and lane 9, G56 with unlabeled IGF-I; lanes 10 & 11, G80G81 and lane 12, G80G81 with unlabeled IGF-I.

Again, a clear reduction in binding was evident with the nonconserved G56 mutation ("G56"), and abolished with nonconserved G80G81 double mutant ("G80G81") (FIG. 6, lower panel). The binding of $^{125}$I-IGF-I to the G56 mutant was specific, since it could be competed with unlabeled IGF-I. In the affinity cross-linking experiment, proteins were preincubated with [$^{125}$I]-IGF-I in Hepes buffer, cross-linked, and then run on an SDS-PAGE gel, dried and exposed to film.

Figure 7:
FIG. 7 shows a Western blot analysis of the $[^{125}I]$-IGF-I binding affinity of Cos-7 cell-expressed IGFBP-3 mutants of the present invention. The results show decreased binding with nonconservative single amino acid mutations ("G56," "G80" and "G81"), and abolished binding with nonconserved double- and triple-amino acid mutations ("G80G81" and "G56G80G81").
Figure 7:

Cos-7 cell-expressed IGFBP-3 mutants. A Western blot analysis of the [$^{125}$I]-IGF-I binding affinity of Cos-7 cell-expressed IGFBP-3 mutants (I56G, L80G, L81G, L80GL81G double mutant, I56GL80GL81G triple mutant) was performed (FIG. 7). Cos-7 cells were transiently transfected with FLAG-tagged DNA vectors corresponding to: vector alone (control); FLAG-tagged IGFBP-3 mutants; and FLAG-tagged wild-type IGFBP-3. The conditioned media was collected after 48 hours. The medium was immunoprecipitated with the M2 anti-FLAG antibody (i.e., the FLAG-sequence specific monoclonal antibody) prior to analysis, to remove any endogenous IGFBP-3 that may have been produced by the Cos-7 cells. Immunoprecipitated samples were analyzed using 12% SDS-PAGE gel electrophoresis. Western ligand blots were incubated overnight 4° C. with 1×10$^6$ cpm [$^{125}$I]-IGF-I, dried, and exposed to film (that equal amounts of protein were applied was confirmed by Western immunoblot with a polyclonal antibody to IGFBP-3). Lane 1, IGFBP-3; lane 2, G81 mutant; lane 3, pCMV6 vector alone; lane 4, G56 mutant; lane 5, G80 mutant; lane 6, G80G81 mutant; lane 7, G56G80G81 mutant; lane 8, empty; lane 9, rhIGFBP-3.

The results show decreased binding with nonconservative single amino acid mutations ("G56," "G80" and "G81; with G81 least affected), and abolished binding with nonconserved double- and triple-amino acid mutations ("G80G81" and "G56G80G81"). There was no [$^{125}$I]-IGF-I binding with negative controls of conditioned media or vector alone (i.e., CM or pCMV6, respectively). [$^{125}$I]-IGF-I binding with FLAG-tagged recombinant human IGFBP-3 ("rhIGFBP-3$^{FLAG}$" control) was as expected.

Figure 8:
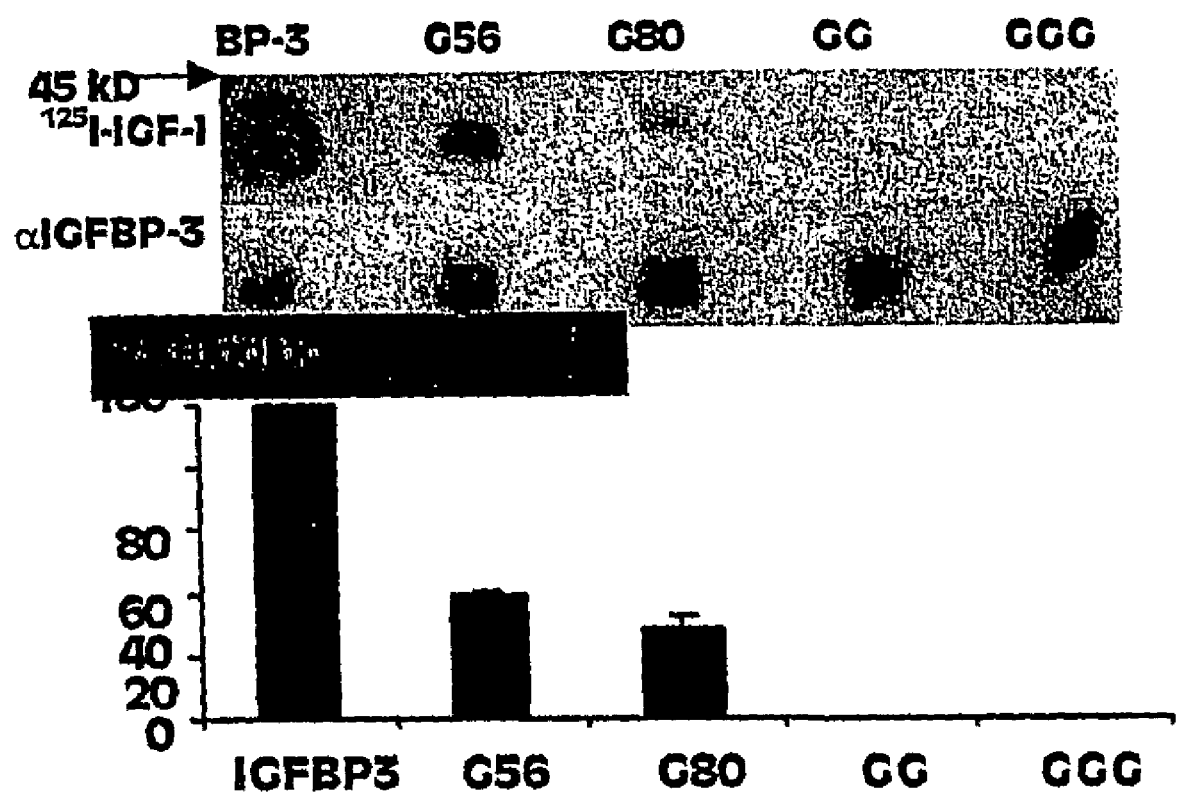
FIG. 8 shows a Western blot analysis of $[^{125}I]$-IGF-I binding affinity of baculovirus-generated IGFBP-3 mutants. A decrease in $[^{125}I]$-IGF-I binding was observed with the nonconservative G56 and G80 mutations ("G56," and "G80"), and binding was completely abolished in the case of the G80G81 and G56G80G81 double and triple nonconservative mutations ("G80G81" and "G56G80G81").

Baculovirus-expressed IGFBP-3 mutants. Based upon the results of the above described screening binding studies, a Western blot analysis of [$^{125}$I]-IGF-I binding affinity of baculovirus-generated IGFBP-3 mutants (I56G, L80G, L80GL81G double mutant, I56GL80GL81G triple mutant) was performed (FIG. 8). FLAG-tagged mutant proteins were expressed using a baculovirus expression system, purified using a M2 antibody (anti-FLAG) column. Purity of pooled fractions was verified by silver stain of protein subjected to SDS-PAGE, and quantitated (relative to known quantities of Baculovirus-generated hIGFBP-3) by Coomassie staining and IRMA assay. Protein binding of [$^{125}$I]-IGF-I was analyzed by Western ligand blot analysis.

Briefly, fifty (50) ng of purified protein was loaded and run on 12% SDS-PAGE, incubated overnight with 1×1$^6$ cpm $^{125}$I-IGF-I (upper panel). Corresponding immunoblot probed with anti-IGFBP-3 antibody (lower portion of upper panel). Lane 1, IGFBP-3; lane 2, G56 mutant; lane 3, G80 mutant; lane 4, G80G81 mutant (double G); lane 5, G56G80G81 mutant (triple G).

The mutations introduced did not interfere with the ability of the peptide to be recognized by the anti-IGFBP-3 antibodies used in the assay, and parallel curves of the mutants were generated with each assay run, suggesting minimal disruption of the tertiary structure and of the epitopes recognized by the antibodies.

Bands detected by Western ligand analysis (FIG. 8, upper panel) were quantified by densitometry (FIG. 8, lower panel graph) to determine mean percent binding, assuming wild-type IGFBP-3 to be 100%. At least three separate experiments were performed with error bars representing +1 SD. The densitometry data showed a 60% reduction in binding of [$^{125}$I]-IGF-I for G56, a 70% reduction for G80, and a reduction to background level for the double G and triple G mutants. No binding was seen for the double G or triple G mutants ("G80G81" and "G56G80G81"), even with long exposures of up to one week. Similar levels of binding were seen when the ligand used was IGF-II. Verification of protein quantity loaded (50 ng/lane) was made by immunoblot with anti-IGFBP-3 monoclonal antibody (FIG. 8, lower panel). Similar quantitation results for mutant proteins were observed on immunoblots using an anti-IGFBP-3 polyclonal antibody produced in our laboratory (data not shown).

in mutants G56 and G80. However, the double G and the triple G mutants still showed little, if any, binding.

BIAcor™ binding affinity measurements. BIAcore™ biosensor measurements (see under "Materials and Methods," above) confirmed the above binding results, providing kinetic affinity data for the various IGFBP-3 mutants. Native and the four glycine mutant IGFBP-3 proteins were each covalently bound to a gold biosensor chip, and increasing concentrations of IGF-I or -II were used in the buffer flow.

TABLE II shows the kinetic parameters determined by this methodology. Wild-type IGFBP-3 was found to have a $K_D$ of $0.79 \times 10^{-9}$ for IGF-I and $0.69 \times 10^{-9}$ for IGF-II. Relative to wild-type, the G56 mutant was found to have a 1.7-fold lower affinity for IGF-I, while the G80 mutant had a 4.3-fold lower affinity for IGF-I, with statistically significant increases in the dissociation rates. Both single mutants preserved normal affinity for IGF-II. The double G mutant had only minimal binding to IGF-I and -II, at least 3- to 4-orders of magnitude lower affinity. The triple G mutant had no detectable binding of either IGF-I or IGF-II.

TABLE II

BIAcore ™ Analysis

| Analyte | Ligand | Mean $k_{on}$ $10^6$/Ms | 95% CI $k_{on}$ | Mean $k_{off}$ 1/s | 95% CI $k_{of}$ | $K_A$ 1/M | $K_D$ nM |
|---|---|---|---|---|---|---|---|
| IGFBP-3 | IGF-I | 0.681 | 1.25-12.37 | $5.36 \times 10^{-4}$* | 4.56-6.16 | $1.27 \times 10^9$ | 0.79 |
|  | IGF-II | 0.791 | 4.62-11.20 | $5.50 \times 10^{-4}$ | 5.13-5.87 | $1.44 \times 10^9$ | 0.69 |
| G56 | IGF-I | 0.696 | 4.33-9.59 | $9.35 \times 10^{-4}$* | 8.81-9.89 | $0.75 \times 10^9$ | 1.34 |
|  | IGF-II | 1.18 | 7.44-16.16 | $3.76 \times 10^{-4}$ | 2.25-5.27 | $3.15 \times 10^9$ | 0.32 |
| G80 | IGF-I | 0.368 | 0.43-6.93 | $12.5 \times 10^{-4}$* | 8.92-16.08 | $0.294 \times 10^9$ | 3.40 |
|  | IGF-II | 1.33 | 2.9-23.7 | $3.85 \times 10^{-4}$ | 0.65-7.05 | $3.45 \times 10^9$ | 0.29 |

Figure 9:
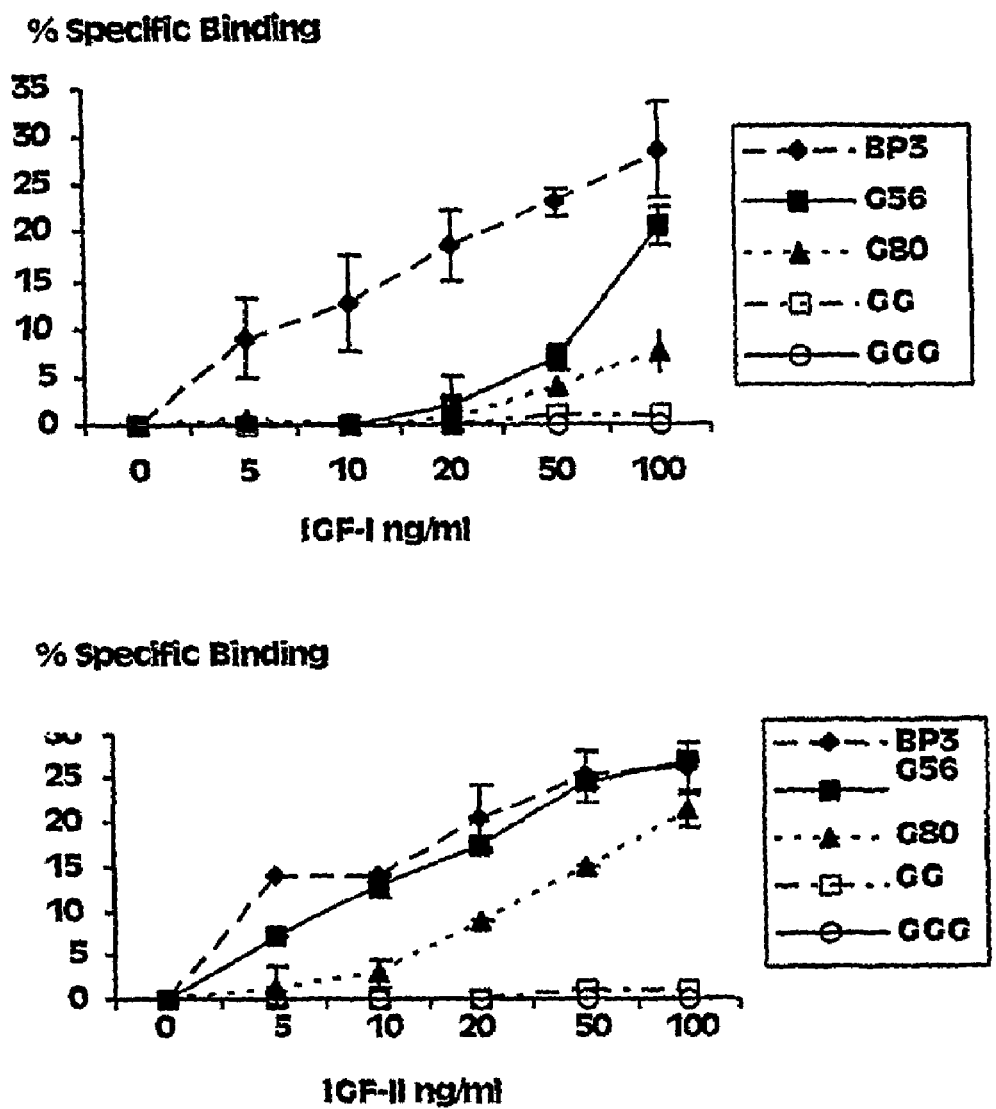
FIG. 9 shows a [$^{125}$I]-IGF-I solution binding assay using baculovirus-generated IGFBP-3 mutant proteins. Compared with [$^{125}$I]-IGF-I binding to wild-type IGFBP-3 ("BP-3"), there was a decrease in specific IGF binding for G56 ("G56"), a larger decrease for G80 ("G80"), very little binding for G80G81 ("GG"), and no significant binding for G56G80G81 ("GGG").

Solution binding assay using Baculovirus-expressed IGFBP-3 mutants. Solution binding assays were more sensitive than ligand blots for determining binding of IGF-I and -II by the mutants. A [$^{125}$I]-IGF-I solution binding assay using baculovirus-generated IGFBP-3 mutant proteins (I56G, L80G, L81G, L80GL81G double mutant, I56GL80GL81G triple mutant) was performed to confirm and further characterize mutant IGFBP-3 binding to IGF (FIG. 9). A charcoal solution binding assay was performed to determine the binding affinity of the IGFBP-3 mutants of the present invention. Specifically, zero (0) to 100 ng/ml of IGFBP-3, wild-type or mutants was incubated overnight at 4° C. in 0.5 ml solution with 10,000 cpm [$^{125}$I]-IGF-I. Activated charcoal solution was added for 15 minutes to absorb any free [$^{125}$I]-IGF-I, and then removed by low-speed centrifugation for 30 minutes. [$^{125}$I]-IGF-I that was bound to protein in the supernatant fraction was counted with gamma counter. The % specific binding was plotted against the protein weight (nanograms/ml of protein). Experiments were performed in duplicate at least two or three separate times. Graph represents mean % specific binding, and error bars show +/− SD.

FIG. 9 (upper panel) shows that compared with [$^{125}$I]-IGF-I binding to wild-type IGFBP-3 ("BP-3"), there was a decrease in specific IGF binding for G56 ("G56"), a larger decrease for G80 ("G80"), very little binding for G80G81 ("GG"), and no significant binding for G56G80G81 ("GGG").

FIG. 9 (lower panel) shows that differences in affinity for IGF-I and -II were more apparent by this method; specifically, the affinity for IGF-II was less affected than for IGF-I Table II. BIAcore Analysis; summary of kinetic data Native and mutant IGFBP-3 species were immobilized on the biosensor chips (see "Materials and Methods"). Six concentrations of IGF-I and -II were passed over each chip. A 1:1 mass transfer curve-fitting model was used in the evaluation. The affinity measurements were done in triplicates, and the mean $k_{on}$ and $k_{off}$ with 95% confidence intervals (CI) were calculated. The $K_A$ value was obtained by dividing $k_{on}$ with $k_{off}$, and the $K_D$ value by taking the inverse of $K_A$. IGF-I and IGF-II only minimally bound to the double G mutant, at least 3-4 orders of magnitude lower affinity. The IGFs did not bind the triple G mutant at all. The off-rates* of IGF-I bound to the native IGFBP-3, G56, and G80 chips were the only significant changes as calculated by a one way ANOVA performed in the Sigma Stat program.

IGF-dependent actions of IGFBP-3 and mutants mirror IGF affinity. IGFBP-3 is known to inhibit the IGF-I-stimulated phosphorylation of the type I IGF receptor (IGF-IR) when added to culture medium (Clemmons, D. R., *Cytokine Growth Factor Rev.* 8:45-62, 1997). Thus, the ability of the present mutant IGFBP-3 species to modulate this IGF-dependent action, based on their varying affinities for IGF, was determined.

Figure 11:
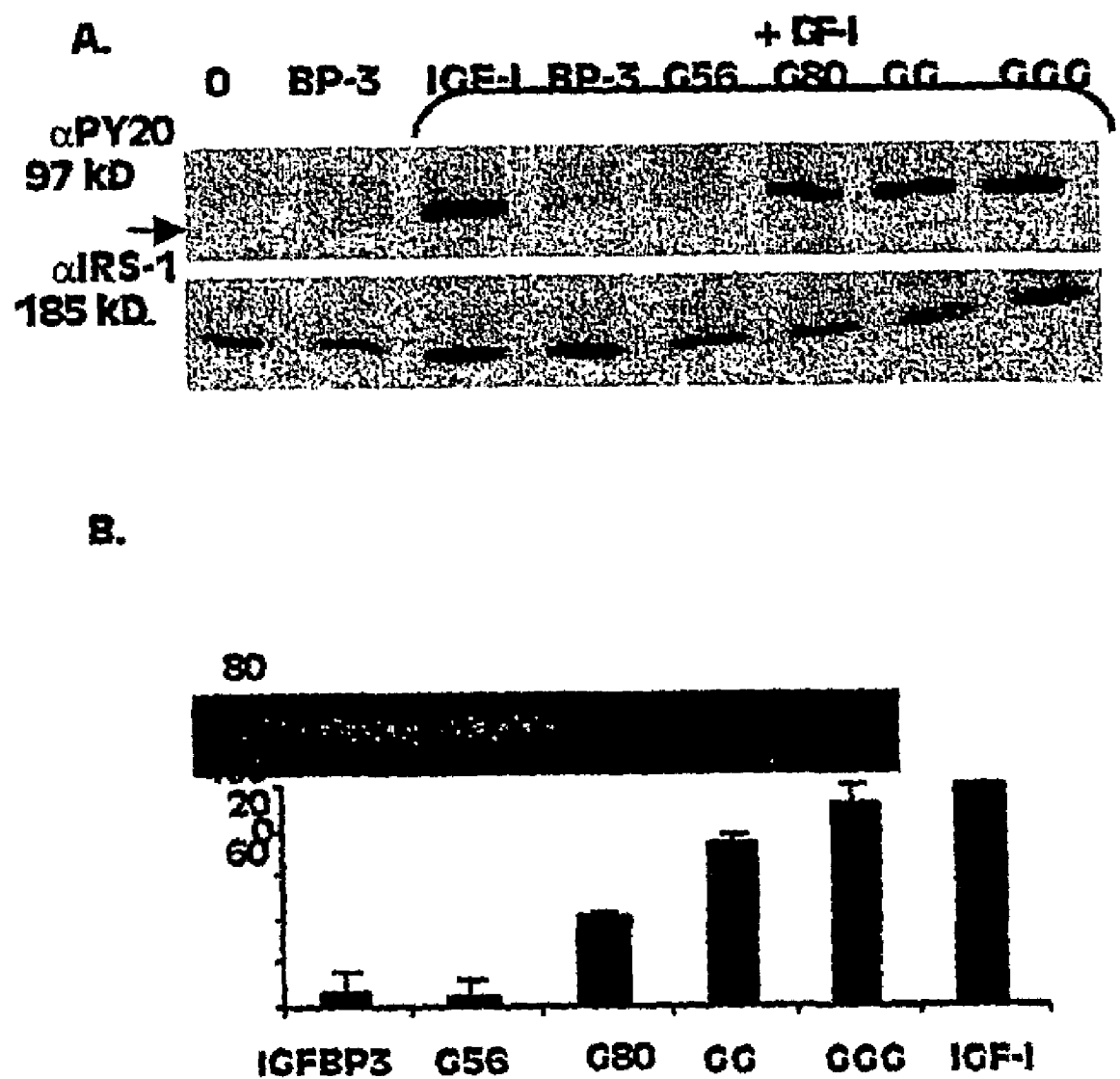
FIG. 11 (upper panel; "A") shows that tyrosine phosphorylation of the β-subunit of the IGF-IR was seen when Cos-7 cells were treated with 100 ng/ml of IGF-I, but was blocked when the IGF-I and 250 ng/ml of wild-type IGFBP-3 were preincubated and then used to treat the cells. Likewise, the G56 mutant still bound IGF-I with sufficient affinity to inhibit the phosphorylation. Less inhibition of IGF-IR phosphorylation was seen with the other three mutants relative to the degree of loss of IGF affinity; using the triple G mutant, no significant inhibition was observed. The graph lower panel; "B") represents the mean densitometric values of three separate experiments +1 SD of the percent IGF-I stimulated phosphorylation of the beta-subunit of the type I IGF-R, quantified from the immunoblots, assuming IGF-I alone stimulates 100%. The affinity of the mutants for IGF was reflected in the degree of inhibition of IGF-stimulated phosphorylation of the receptor.

Briefly, confluent monolayers of NIH-3T3 fibroblasts were serum-starved overnight and treated for 10 min with 100 ng/ml IGF-I alone or after preincubation with 250 ng/ml IGFBP-3 wild-type or mutant protein for 30 min at 21 C. Cell lysates were collected, and equal amounts of protein were run under reducing conditions on 8% SDS-PAGE. Phosphorylation of the beta subunit of the type I IGF-I receptor was probed with anti-PY20 antibody (upper panel), and equal protein loading was confirmed by immunoblot for anti-IRS-1 antibody (FIG. 11, lower portion of upper panel). Lane 1, no treatment; lane 2, IGFBP-3 alone; lane 3, IGF-I alone; lane 4, IGFBP-3+IGF-I; lane 5, G56+IGF-I; lane 6, G80+IGF-1; lane 7, double G+IGF-I; lane 8, triple G+IGF-1.

FIG. 11 (upper panel) shows that tyrosine phosphorylation of the β-subunit of the IGF-IR was seen when Cos-7 cells were treated with 100 ng/ml of IGF-I, but was blocked when the IGF-I and 250 ng/ml of wild-type IGFBP-3 were preincubated and then used to treat the cells. Likewise, the G56 mutant still bound IGF-I with sufficient affinity to inhibit the phosphorylation. Less inhibition of IGF-IR phosphorylation was seen with the other three mutants relative to the degree of loss of IGF affinity; using the triple G mutant, no significant inhibition was observed (FIG. 11).

The graph (FIG. 11, lower panel) represents the mean densitometric values of three separate experiments +1 SD of the percent IGF-I stimulated phosphorylation of the beta-subunit of the type I IGF-R, quantified from the immunoblots, assuming IGF-I alone stimulates 100%. The affinity of the mutants for IGF was reflected in the degree of inhibition of IGF-stimulated phosphorylation of the receptor.

EXAMPLE 4

Nonconserved Mutant IGFBP-3 Molecules had Either Reduced, or Showed Abolished Binding to IGF, Yet Retained Their Ability to Bind to IGFBP-3 Receptor (P4.33)

The above-described mutations in the IGFBP-3 protein, which reduced or abrogated IGF binding, did not abrogate the ability of these same mutant IGFBP-3-proteins to associate with the IGFBP-3 receptor.

Figure 10:
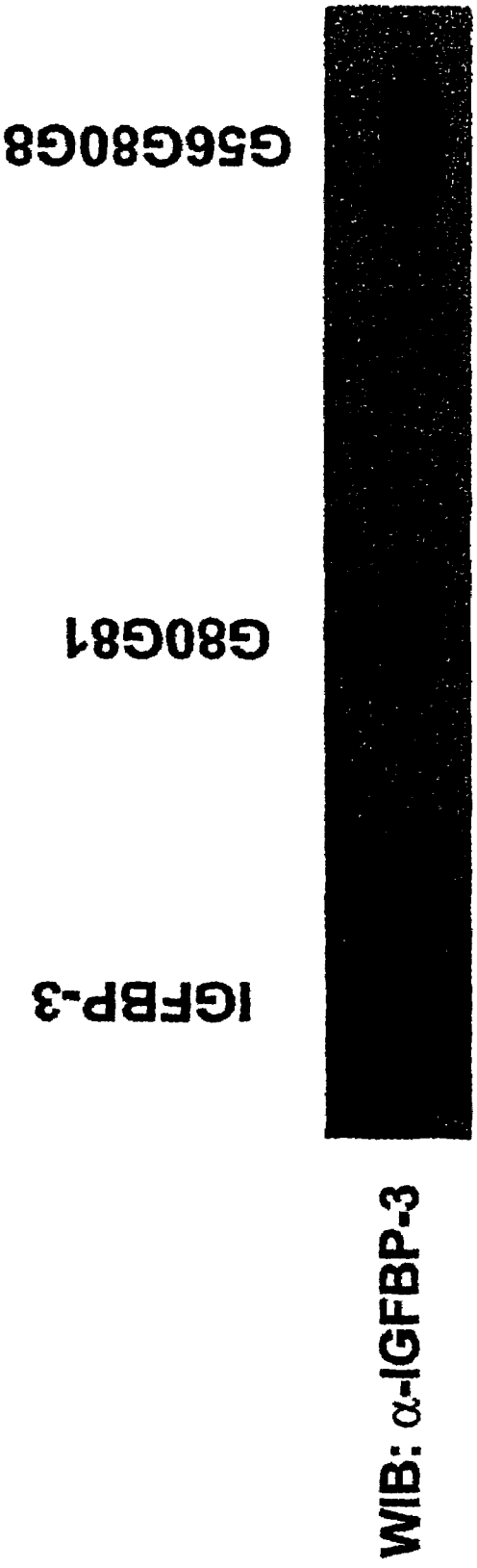
FIG. 10 shows a Western immunoblot analysis of IGFBP-3 mutant protein binding to IGFBP-3 receptor (P4.33; see PCT/US01/1 6437, incorporated by reference herein in its entirety). The experiment shows that mutations in the IGFBP-3 protein, which abrogated IGF binding, did not affect the ability of these same mutant IGFBP-3 proteins to associate with the receptor (produced in Hs578T breast cancer cells).

A Western immunoblot analysis of IGFBP-3 mutant protein binding to IGFBP-3 receptor (P4.33; see PCT/US/01, 16437) was performed (FIG. 10).

Hs578T breast cancer cells were transiently transfected with an IGFBP-3 receptor construct, EGFP:4-33. Cell lysates were collected after 48 hours, incubated with either wild-type or IGFBP-3 mutants (L80GL81G double mutant, and I56GL80GL81G triple mutant), and immunoprecipitated with antibody to GFP. Samples were analyzed on an SDS-PAGE gel under reducing conditons, and anti-IGFBP-3 monoclonal antibody was used to detect protein using a standard Western immunoblot procedure.

The data of FIG. 10 shows that mutations in the IGFBP-3 protein that abrogated IGF binding, did not abrogate the ability of these same mutant IGFBP-3 proteins to associate with the IGFBP-3 receptor (P4.33).

EXAMPLE 5

IGFBP-3 Regulated the Number of Undifferentiated Chondrocytic Cells through the Regulation of Apoptosis The above-described mutations in the IGFBP-3 protein, which reduced or abrogated IGF binding, did not abrogate the ability of these same mutant IGFBP-3 proteins to associate with the IGFBP-3 receptor. These mutants thus represent unique tools to investigate the IGF-independent biological effects of IGFBP-3 in the process of chondrogenesis, which is not well understood.

Although there is some support that IGFBP-3 has an IGF-independent anti-proliferative effect in undifferentiated and early differentiated chondrocytes, but not in terminally differentiated chondrocytes (Spagnoli et. al., *J. Biol. Chem.* 276:5533-5540, 2001), the affects on differentiation and on the precise cell types involved are not well understood.

Accordingly, the art-recognized RCJ3.1C5.18 chondrogenic cell line model (Grigoriadis et al., *Differentiation* 60:299-307, 1996; Lunstrum et al., *J. Histochem. Cytochem.* 47:1-6, 1999; Spagnoli et. al., *J. Biol. Chem.* 276:5533-5540, 2001) was used to: 1) evaluate the IGF-independent effect of IGFBP-3 in RCJ3.1C5.18 chondroprogenitors; and 2) characterize the effect of IGFBP-3 on modulating the rate of chondrocyte differentiation.

Materials and Methods

Cell culture and transfection. RCJ3.1C5.18 cells, generously donated by Dr. Jane E. Aubin (University of Toronto), were plated and grown as previously reported (Spagnoli et. al., *J Biol. Chem.* 276:5533-5540, 2001). Briefly, cells were seeded in MEMα with 15% FBS, 2 mM sodium pyruvate (Gibco-BRL; Gaithersburg, Md.), and 10-7 M dexamethazone (Sigma Chemical; St Louis, Mo.). After reaching confluence and beginning to form chondrocytic nodules (4 days of culture), fresh medium was supplemented with 50 μg/ml of ascorbic acid (Wako Pure Biochemicals Industries Ltd; Osaka, Japan), and 10 mM β-glycerophosphate (Sigma). Cells grown in this manner undergo a reproducible, time-dependent progression from chondroprogenitors to hypertrophic chondrocytes over 14 days of culture (Lunstrum et al., *J. Histochem. Cytochem.* 47:1-6, 1999; Spagnoli et. al., *J. Biol. Chem.* 276:5533-5540, 2001).

For transfection, hIGFBP-3 and IGFBP-3 mutant cDNAs were subcloned into the pCMV6 vector, as previously described (Buckway et al., *J. Clin. Endocrinol. Metab. in press,* 2001). Cells were seeded in 6-well dishes and 24 hours later were transfected with 4 μg of expression vector plasmid using Mirus Transit LT-1 as described by the manufacturer (PanVera; Madison, Wis.).

Measurement of cell apoptosis and cell number. An ELISA kit that detects cytoplasmic histone-associated DNA fragments was used to measure apoptosis 6, 12, 24 and 48 hours after transfection, following the manufacturer's instructions (Roche; Mannheim, Germany). Cell number was determined at the same time points by counting trypsinized cells in a hemocytometer.

RNA isolation and Northern blotting analysis. Total RNA was extracted from cells cultured for 7 days, using RNeasy columns as described by the manufacturer (Qiagen Inc.; Santa Clarita, Calif.). Ten μg of RNA were subjected to Northern Blotting analysis as previously described (Spagnoli et. al., *J. Biol. Chem.* 276:5533-5540, 2001). A mouse type II collagen probe (Salminen et al., *Arthritis Rheum.* 44:947-55, 2001), was generously donated by Dr. Eero Vuorio.

Quantitative proteoglycan(PG) synthesis assay. PG synthesis was quantified by Alcian blue staining as previously described (Grigoriadis et al., *Differentiation* 60:299-307, 1996). Briefly, 7-day-old cell monolayers were stained with Alcian blue (1% in 3% acetic acid), washed and solubilized in 1% SDS, and absorbance determined at 605 nm.

Measurement of IGFBP-3 and GGG mutant. Conditioned media were obtained 6, 12, 24 and 48 hours after transfection. Media were concentrated 7-10 fold using Centricon 3 (Amicon; Boston, Mass.) and IGFBP-3 concentrations were determined using a commercial IRMA kit (Diagnostic Systems Laboratories Inc.; Webster, Tex.).

Statistics. Data are presented as mean±SD. Statistical differences between means were assessed by ANOVA. Statistical significance was set at $p<0.05$.

Results

Figure 12:
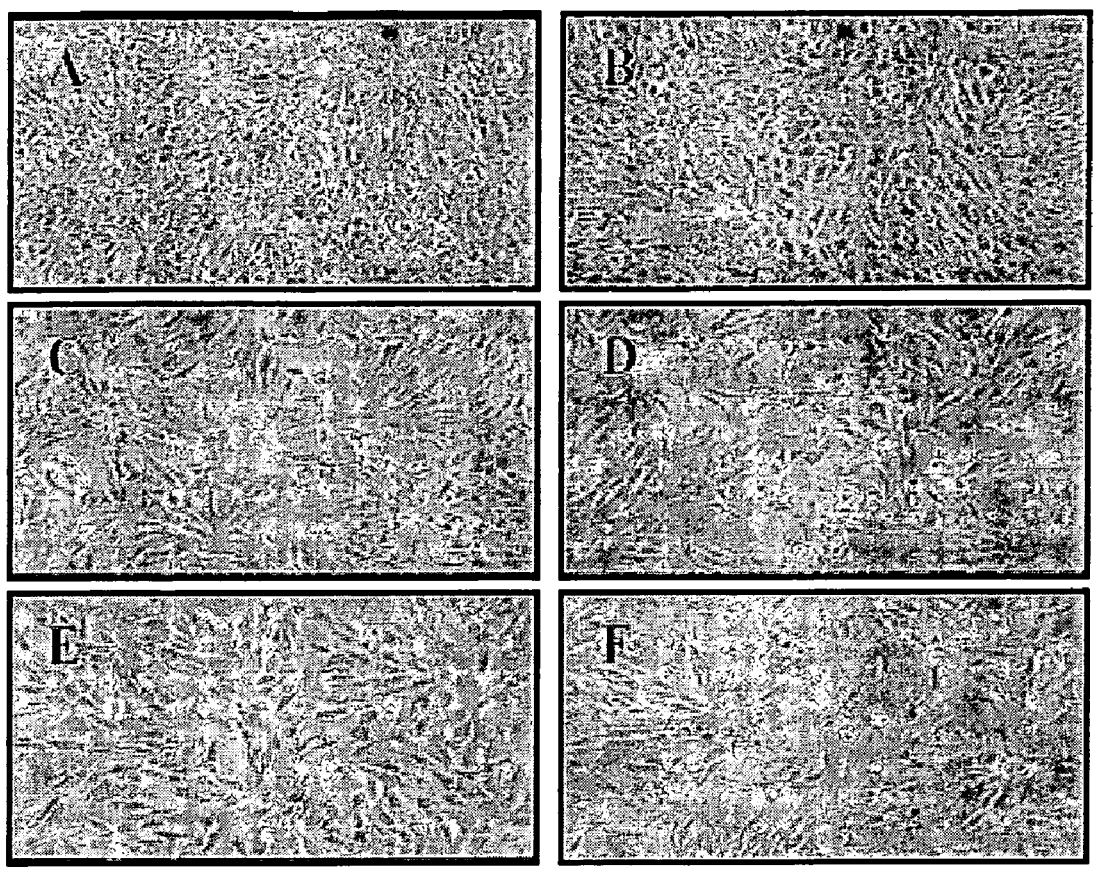
FIG. 12 shows, according to the present invention, IGF-independent effects of IGFBP-3 on RCJ3.1C5.18 cell morphology. RCJ3.1C5.18 cells were transfected with empty vector (B), IGFBP-3 (C), G mutant (D), GG mutant (E) or GGG mutant (F). Panel A shows untransfected cells.

IGF-independent effect of IGFBP-3 on chondroprogenitors. Remarkable cell morphology changes were noted after transfection of undifferentiated RCJ3.1C5.18 cells with IGFBP-3 or IGFBP-3 mutants (FIG. 12). FIG. 12 shows independent effects of IGFBP-3 on RCJ3.1C5.18 cell morphology. RCJ3.1C5.18 cells were transfected with empty vector (B), IGFBP-3 (C), G mutant (D), GG mutant (E) or GGG mutant (F). Panel A shows untransfected cells. RCJ3.1C5.18 cells transfected with either mutant or wild-type IGFBP-3 detached and lost their characteristic cuboidal phenotype 24 hours after transfection.

In the media of cells transfected with IGFBP-3 or GGG, up to 70 ng/ml IGFBP-3 and 60 ng/ml GGG mutant were measured,. with maximal levels 24 hours after transfection.

Figure 13:
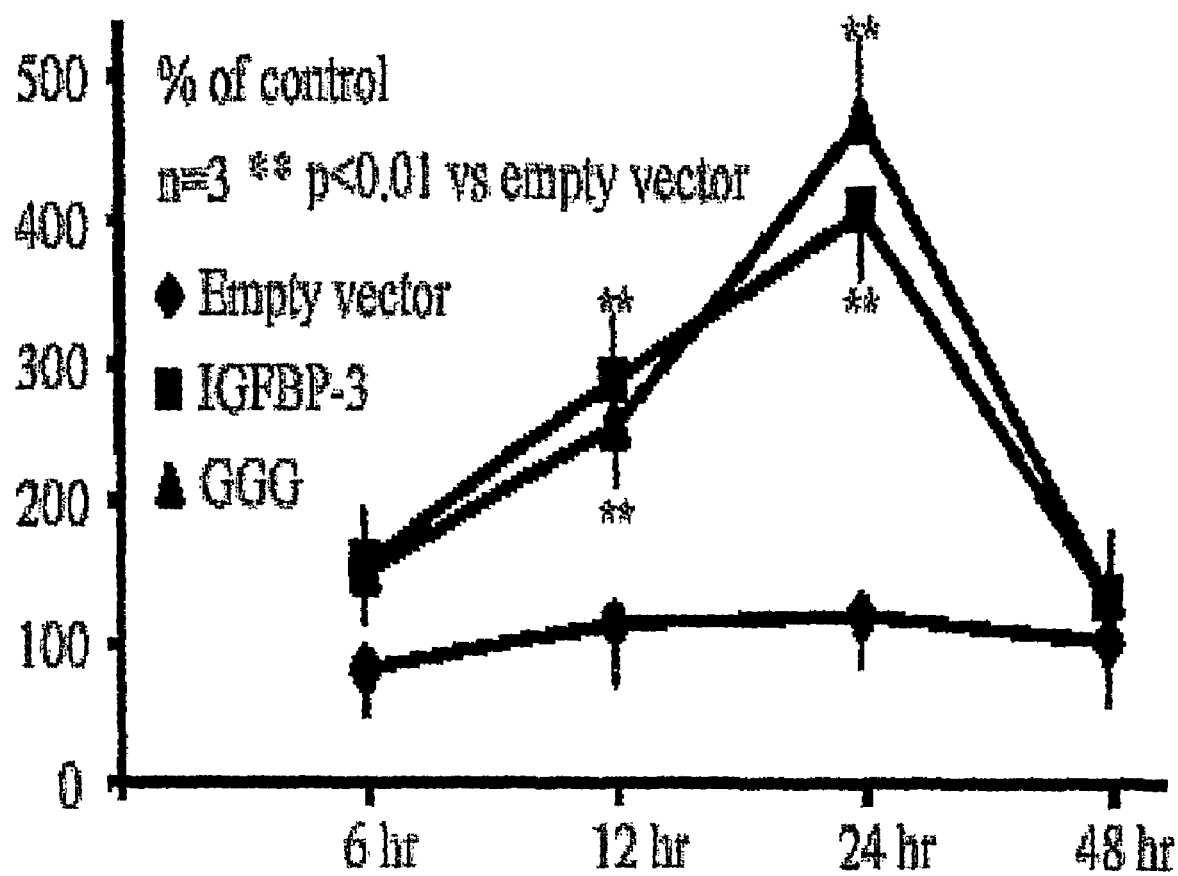
FIG. 13 shows, according to the present invention, that IGFBP-3 induces apoptosis in RCJ3.1C5.18 cells. Apoptosis was determined at different times after transfection using an ELISA kit (Example 5, "Materials and Methods"). Results are expressed as percentage of the apoptosis measured in untransfected control cells.

IGF-independent effect of IGFBP-3 on induction of apoptosis in chondroprogenitors. FIG. 13 shows that RCJ3.1C5.18 cells transfected with IGFBP-3 or the GGG mutant gradually underwent apoptosis, with a maximal effect 24 hours after transfection (~400 to ~500% of untransfected control). Apoptosis was determined at different times after transfection using an ELISA kit (Example 5, "Materials and Methods"). Results are expressed as percentage of the apoptosis measured in untransfected control cells.

Figure 14:
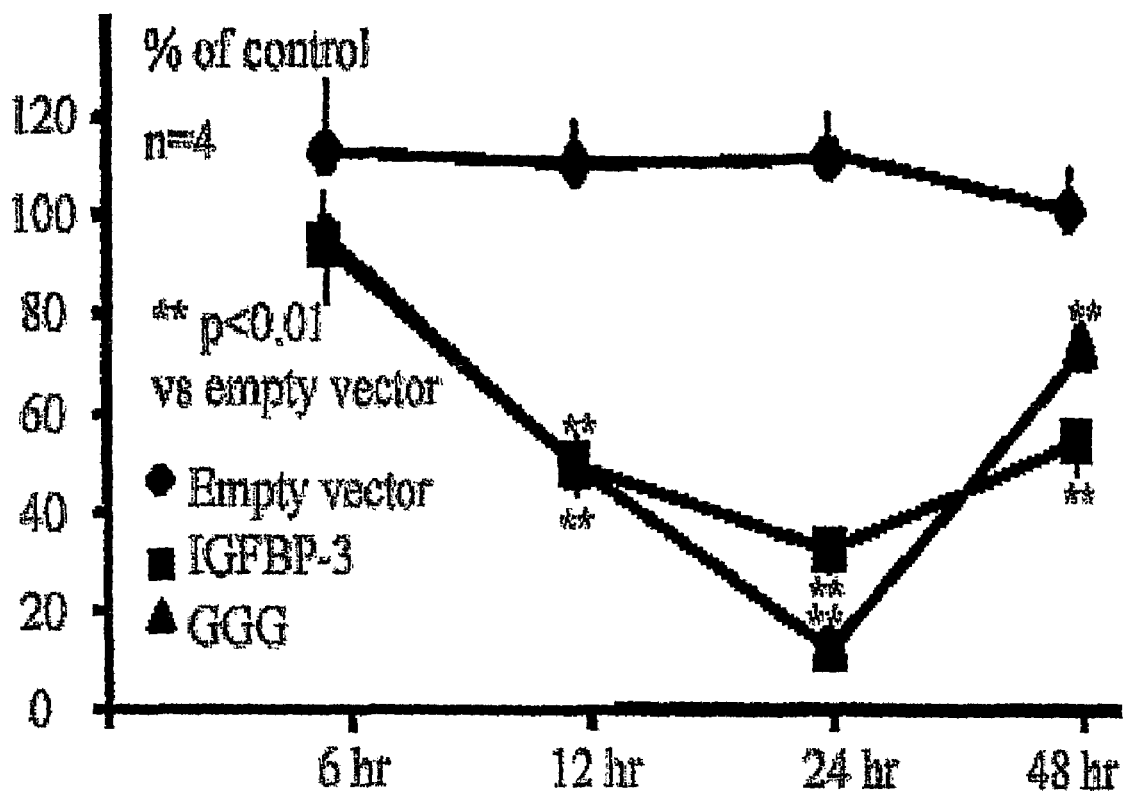
FIG. 14 shows, according to the present invention, the IGFBP-3 effect on cell number during the corresponding apoptosis assay of FIG. 13. RCJ3.1C5.18 cell number was determined at different time points after transfection and expressed as percentage of the number of untransfected control cells.

At the same time point, cells transfected with IGFBP-3 or GGG reached the lowest cell number (~30 to ~10% of control) (FIG. 14). Forty-eight hours after transfection with IGFBP-3 or GGG, cells resumed their growth, as indicated by an increase in cell number (FIG. 14). RCJ3.1C5.18 cell number was determined at different time points after transfection and expressed as percentage of the number of untransfected control cells.

Figure 15:
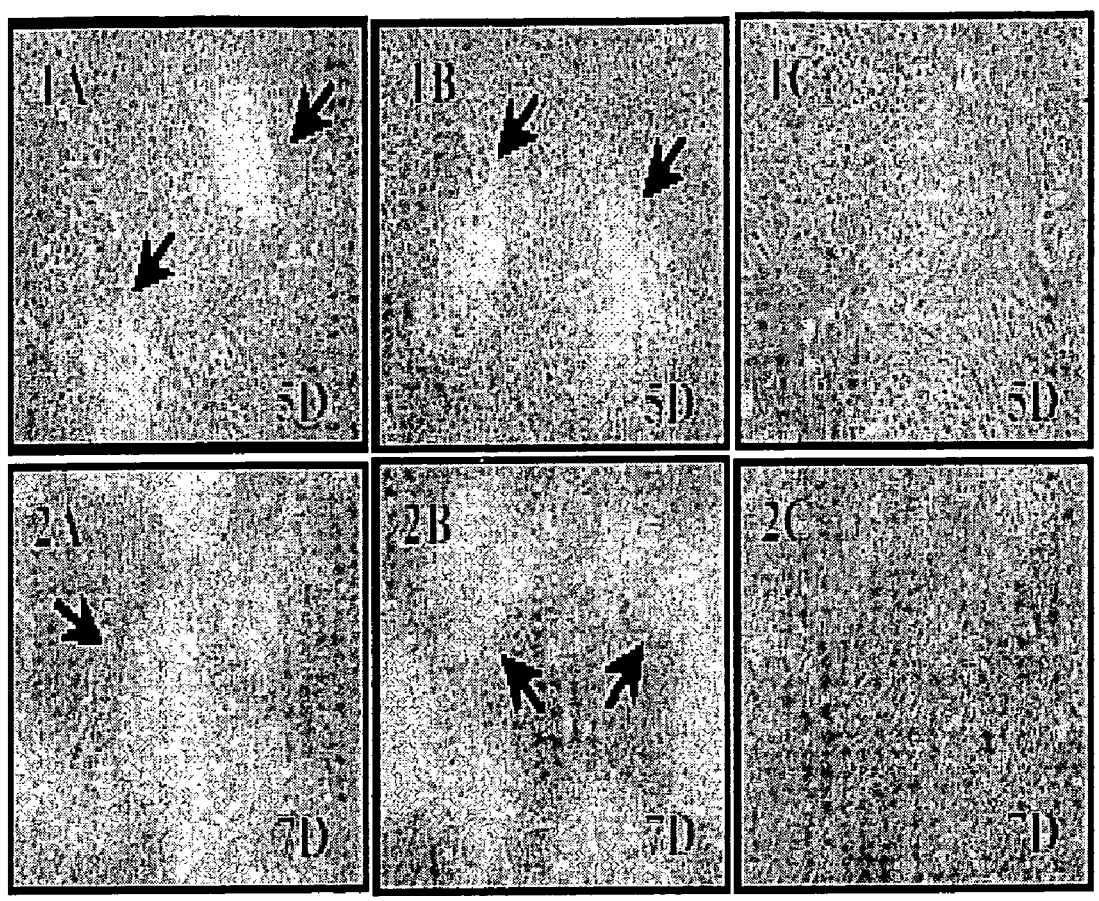
FIG. 15 shows, according to the present invention, the selective effect of IGFBP-3 on the differentiation of chondroprogenitors. Cells are depicted at 5 days (5D) and 7 days (7D) of culture; transfected with empty vector (panels 1B, 2B) or with IGFBP-3 (panels 1C, 2C); panels 1A and 2A show untransfected cells.

IGF-independent effect of IGFBP-3 on chondrocyte maturation and differentiation. FIG. 15 depicts 5 and 7 day old RCJ3.1C5.18 cells, studied 4 and 6 days after transfection. Cells transfected with IGFBP-3 continued growth (panel 1C) and reached confluence (panel 2C), but did not form chondrocytic nodules (indicated by arrows), as did untransfected panels 1A and 2A) or empty vector-transfected cells (panels 1B and 2B). Significantly, these results indicate that the IGFBP-3 effect was selective on the cell population of chondroprogenitors that was committed to become differentiated chondrocytes. A similar effect was noted when cells were transfected with the GGG IGFBP-3 mutant.

To confirm this selective effect of IGFBP-3 on chondrocyte maturation, type II collagen expression and PG proteoglycan) synthesis were measured, as markers of chondrocyte differentiation. As determined at 7 days of culture, transfection of undifferentiated cells with either IGFBP-3 or the GGG mutant induced at least a 50% decrease of type II collagen gene expression FIG. 16) and PG synthesis (FIG. 17), compared to cells untransfected or transfected with empty vector.

Figure 16:
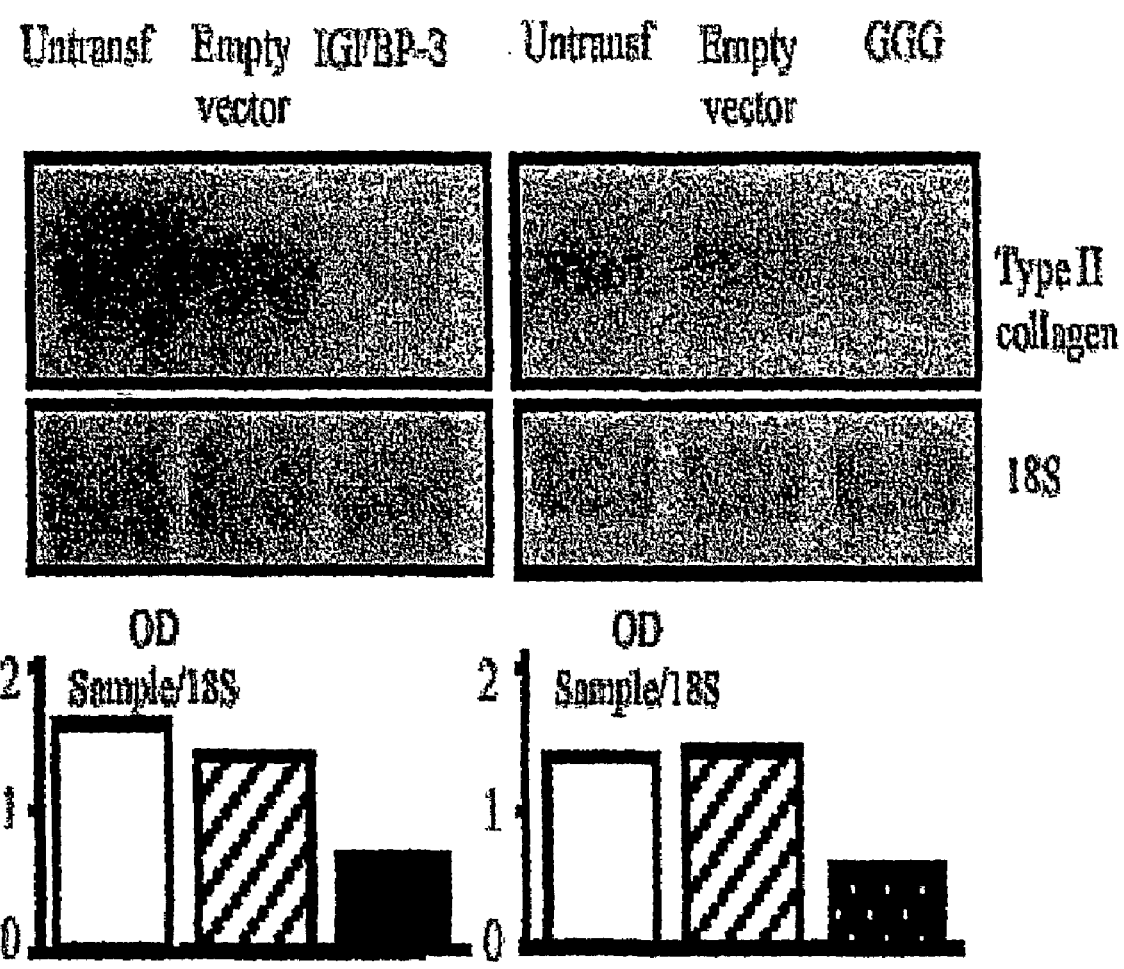
FIG. 16 shows, according to the present invention, IGF-independent effect of IGFBP-3 on type II collagen expression. Total RNA obtained from cells cultured for 7 days and transfected 24 hours after seeding was subjected to Northern blotting analysis. Type II collagen mRNA levels were normalized for 18S rRNA levels.
Figure 17:
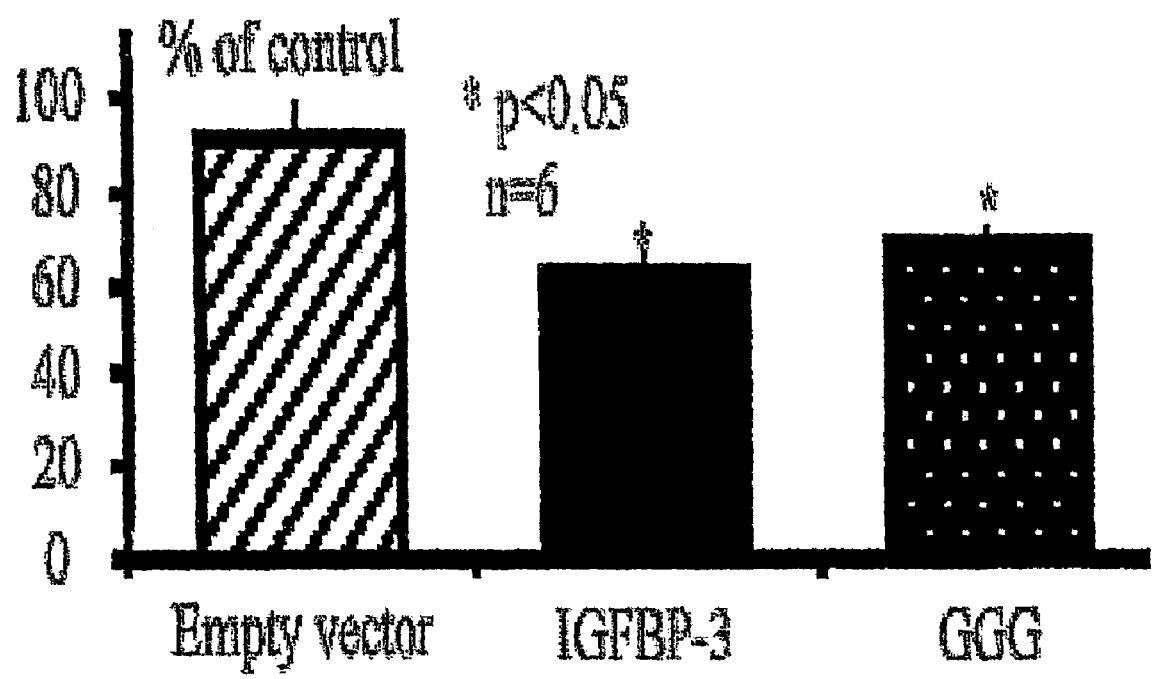
FIG. 17 shows, according to the present invention, IGF-independent effect of IGFBP-3 on PG synthesis. PG synthesis was determined at 7 days culture in cells transfected 24 hours after seeding, using quantitative Alcian blue assay. Results are expressed as percentage of absorbance measured in untransfected control cells.

FIG. 16 shows the IGF-independent effect of IGFBP-3 on type II collagen expression. Total RNA obtained from cells cultured for 7 days and transfected 24 hours after seeding was subjected to Northern blotting analysis. Type II collagen mRNA levels were normalized for 18S rRNA levels. FIG. 17 shows the IGF-independent effect of IGFBP-3 on PG synthesis. PG synthesis was determined at 7 days culture in cells transfected 24 hours after seeding, using quantitative Alcian blue assay. Results are expressed as percentage of absorbance measured in untransfected control cells.

In Summary for this Example. A novel IGF-independent role for IGFBP-3 was identified. IGFBP-3 regulates the number of undifferentiated chondrocytic cells through the regulation of apoptosis. This IGFBP-3 effect results in a remarkable loss of chondrocytic nodule formation, that is associated with a significant decrease of type II collagen expression and PG synthesis. IGFBP-3 modulates chondrogenesis by selectively controlling the number of chondroprogenitors committed to undergo differentiation.

Thus, according to the present invention, an IGF-independent apoptotic effect of IGFBP-3 is physiologically relevant in chondrogenesis. The inhibitory effect of IGFBP-3 on chondroprogenitors contributes to the modulation of the differentiation process. The control of skeletal development is a complex phenomenon, and the current data support a novel role for IGFBP-3 in this process.

SUMMARY

The existence of an N-terminal hydrophobic region that is important for IGF binding has been previously postulated (see "Background," above). Additionally, most investigators agree that both the N-terminus and the C-terminus of the IGFBPs are required to be in the appropriate conformation, stablized by disulfide bonds, for high-affinity IGF binding to occur.

However, for purposes of IGF-independent functions, these studies do not teach or suggest which amino acids within the N-terminus of IGFBPs have singularly, or in combination, the most effect on IGF affinity, without altering the disulfide bonds of these cysteine-rich binding proteins so as to preserve IGF-independent activities.

According to the present invention, particular amino acids in the N-terminal region of IGFBPs contribute to a primary N-terminal IGF binding site, without abrogating IGFBP-3 receptor binding. Specifically, compared with $[^{125}I]$-IGF-I binding to wild-type IGFBP-3 ("BP-3"), there was a decrease in specific IGF binding for G56 ("G56"), a larger decrease for G80 ("G80"), very little binding for G80G81 ("GG"), and no significant binding for G56G80G81 ("GGG"). Significantly, however, mutations in the IGFBP-3 protein that abrogated IGF binding (G80G81 and G56G80G81), did not abrogate the ability of these same mutant IGFBP-3 proteins to associate with the IGFBP-3 receptor (P4.33).

Valine is a large, nonpolar amino acid, as are isoleucine and leucine. When valine was substituted for either isoleucine or leucine, it did not affect binding dramatically. However, when glycine, a small, polar residue, was used instead of valine, it produced very different results, with more marked reductions in binding, suggesting that a change from hydrophobic to nonhydrophobic residues was more relevant than the amino acid itself.

Binding studies using purified Baculovirus-generated protein showed that the substitution of glycine for leucine at position 80 led to the single greatest reduction in affinity, and furthermore, only two mutations (double G mutant) were necessary to abolish binding completely to both IGF-I and -II by Western ligand blot. On more sensitive solution binding assays, binding was still not detected for the double G or the triple G mutant.

BIAcore analysis further validated these findings, and provided kinetics data supporting a loss of affinity by the mutants. The lower affinities of the G56 and the G80 mutants for IGF-I were statistically significant for increased rates of dissociation, indicating that although IGF-I is able to bind these mutants, the complexes are possibly not as stable as wild-type IGFBP-3. Interestingly, IGF-II binding was not affected for the single mutations. However, for both IGF-I and -II, there was absolutely no binding detectable for the triple G mutant and only very minimal binding for the double G mutant.

According to the present invention the above-described mutant IGFBP-3 species reduce or eliminate IGF binding without significant alteration of tertiary structure of the IGFBP protein. The mutant proteins were easily detectable on immunoblot by both a rabbit anti-IGFBP-3 polyclonal antibody and a monoclonal anti-IGFBP-3 antibody, suggesting that no disruption of the epitopes recognized by these antibodies occurred. Similarly, the quantity of the mutants was accurately measured by an IRMA assay that utilized a goat anti-IGFBP-3 polyclonal antibody, and with each assay run, curves of dilutions of mutants and native IGFBP-3 remained parallel.

According to the present invention, IGF-dependent actions of IGFBP-3 are via the sequestration of IGF, thereby inhibiting stimulation of the receptor. According to the present invention, this is primarily a function of the N-terminus, rather than the mid-region or C-terminus, as previously thought (Devi G R, et al., *Endocrinology* 141:4171-9, 2000). The present data also relate the degree of affinity for IGF with the degree of inhibition of phosphorylation. The lower the affinity a mutant IGFBP-3 has for IGF, the more IGF is able to access the receptor and activate phosphorylation.

A novel IGF-independent role for IGFBP-3 was identified. IGFBP-3 regulates the number of undifferentiated chondrocytic cells through the regulation of apoptosis. This IGFBP-3 effect results in a remarkable loss of chondrocytic nodule formation, that is associated with a significant decrease of type II collagen expression and PG synthesis. IGFBP-3 modulates chondrogenesis by selectively controlling the number of chondroprogenitors committed to undergo differentiation.

Thus, according to the present invention, an IGF-independent apoptotic effect of IGFBP-3 is physiologically relevant in chondrogenesis. The inhibitory effect of IGFBP-3 on chondroprogenitors contributes to the modulation of the differentiation process. The control of skeletal development is a complex phenomenon, and the current data support a novel role for IGFBP-3 in this process.

The present invention provides for novel mutant IGFBP-3 polypeptides and fragments thereof that have either no binding, or show reduced binding to IGFs, yet retain their ability to bind to P4.33 (the IGFBP-3 receptor). The present invention also provides novel mutant IGFBP-3 cDNA sequences, and novel antibodies against mutant IGFBP-3s. The present invention further provides novel drug candidate screening assays, and diagnostic and therapeutic methods for the treatment of cancer, tumor suppression, and bone growth utilizing mutant IGFBP-3 molecules.

---

We claim:

1. A purified polypeptide, the amino acid sequence of which comprises SEQ ID NO:10, wherein the polypeptide binds to the extracellular domain of the human IGFBP-3 receptor.

2. The purified polypeptide of claim 1, wherein the polypeptide is from 87 to about 264 amino acids in length.

3. The purified polypeptide of claim 1, wherein the polypeptide is, or comprises a recombinant variant of human IGFBP-3, wherein the variant consists of the triple glycine substitutions at amino acid positions 56, 80, and 81 of SEQ ID NO:10.

4. A composition comprising a polypeptide, the amino acid sequence of which SEQ ID NO:10, wherein the polypeptide binds to the extracellular domain of the human IGFBP-3 receptor.

5. The composition of claim 4, wherein the polypeptide is from 87 to about 264 amino acids in length.

6. The composition of claim 4, wherein the polypeptide is, or comprises a recombinant variant of human IGFBP-3, wherein the variant consists of the triple glycine substitutions at amino acid positions 56, 80, and 81 of SEQ ID NO:10.

* * * * *

SEQUENCE LISTING

```
<160> NUMBER OF SEQ ID NOS: 11

<210> SEQ ID NO 1
<211> LENGTH: 54
<212> TYPE: DNA
<213> ORGANISM: artificial sequence
<220> FEATURE:
<223> OTHER INFORMATION: Human IGFBP-3-specific oligonucleotide primer

<400> SEQUENCE: 1
agcgagggcc agccgtgcgg cmkctacacc gaacgttgtg gctccggcct tcgc        54

<210> SEQ ID NO 2
<211> LENGTH: 47
<212> TYPE: DNA
<213> ORGANISM: artificial sequence
<220> FEATURE:
<223> OTHER INFORMATION: Human IGFBP-3-specific oligonucleotide primer

<400> SEQUENCE: 2
gaggcgcgac cgctgcaagc gskgskggac ggccgcgggc tctgcgt               47

<210> SEQ ID NO 3
<211> LENGTH: 87
<212> TYPE: PRT
<213> ORGANISM: Homo sapiens
<220> FEATURE:
<221> NAME/KEY: MISC_FEATURE
<222> LOCATION: (56)..(56)
<223> OTHER INFORMATION: Ile, Val or Gly at this position
<220> FEATURE:
<221> NAME/KEY: MISC_FEATURE
<222> LOCATION: (80)..(80)
<223> OTHER INFORMATION: Leu or Gly at this position
<220> FEATURE:
<221> NAME/KEY: MISC_FEATURE
<222> LOCATION: (81)..(81)
<223> OTHER INFORMATION: Leu or Gly at this position
```

-continued

```
<400> SEQUENCE: 3

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Xaa Tyr Thr Glu Arg Cys Gly Ser Gly
    50                  55                  60

Leu Arg Cys Gln Pro Ser Pro Asp Glu Ala Arg Pro Leu Gln Ala Xaa
65                  70                  75                  80

Xaa Asp Gly Arg Gly Leu Cys
                85

<210> SEQ ID NO 4
<211> LENGTH: 87
<212> TYPE: PRT
<213> ORGANISM: Homo sapiens
<220> FEATURE:
<221> NAME/KEY: MISC_FEATURE
<222> LOCATION: (56)..(56)
<223> OTHER INFORMATION: Ile to Gly variant
<220> FEATURE:
<221> NAME/KEY: MISC_FEATURE
<222> LOCATION: (80)..(80)
<223> OTHER INFORMATION: Leu or Gly at this position
<220> FEATURE:
<221> NAME/KEY: MISC_FEATURE
<222> LOCATION: (81)..(81)
<223> OTHER INFORMATION: Leu or Gly at this position

<400> SEQUENCE: 4

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Gly Tyr Thr Glu Arg Cys Gly Ser Gly
    50                  55                  60

Leu Arg Cys Gln Pro Ser Pro Asp Glu Ala Arg Pro Leu Gln Ala Xaa
65                  70                  75                  80

Xaa Asp Gly Arg Gly Leu Cys
                85

<210> SEQ ID NO 5
<211> LENGTH: 87
<212> TYPE: PRT
<213> ORGANISM: Homo sapiens
<220> FEATURE:
<221> NAME/KEY: MISC_FEATURE
<222> LOCATION: (80)..(80)
<223> OTHER INFORMATION: Leu to Gly variant

<400> SEQUENCE: 5

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Val Cys Ala
            20                  25                  30

Glu Leu Val Arg Glu Pro Gly Cys Gly Cys Cys Leu Thr Cys Ala Leu
        35                  40                  45
```

```
Ser Glu Gly Gln Pro Cys Gly Ile Tyr Thr Glu Arg Cys Gly Ser Gly
    50                  55                  60

Leu Arg Cys Gln Pro Ser Pro Asp Glu Ala Arg Pro Leu Gln Ala Gly
65                  70                  75                  80

Leu Asp Gly Arg Gly Leu Cys
                85

<210> SEQ ID NO 6
<211> LENGTH: 87
<212> TYPE: PRT
<213> ORGANISM: Homo sapiens
<220> FEATURE:
<221> NAME/KEY: MISC_FEATURE
<222> LOCATION: (81)..(81)
<223> OTHER INFORMATION: Leu to Gly variant

<400> SEQUENCE: 6

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Ile Tyr Thr Glu Arg Cys Gly Ser Gly
    50                  55                  60

Leu Arg Cys Gln Pro Ser Pro Asp Glu Ala Arg Pro Leu Gln Ala Leu
65                  70                  75                  80

Gly Asp Gly Arg Gly Leu Cys
                85

<210> SEQ ID NO 7
<211> LENGTH: 87
<212> TYPE: PRT
<213> ORGANISM: Homo sapiens
<220> FEATURE:
<221> NAME/KEY: MISC_FEATURE
<222> LOCATION: (56)..(56)
<223> OTHER INFORMATION: Ile to Gly variant
<220> FEATURE:
<221> NAME/KEY: MISC_FEATURE
<222> LOCATION: (80)..(80)
<223> OTHER INFORMATION: Leu to Gly variant

<400> SEQUENCE: 7

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Tyr Thr Glu Arg Cys Gly Ser Gly
    50                  55                  60

Leu Arg Cys Gln Pro Ser Pro Asp Glu Ala Arg Pro Leu Gln Ala Gly
65                  70                  75                  80

Leu Asp Gly Arg Gly Leu Cys
                85

<210> SEQ ID NO 8
<211> LENGTH: 87
<212> TYPE: PRT
<213> ORGANISM: Homo sapiens
```

-continued

```
<220> FEATURE:
<221> NAME/KEY: MISC_FEATURE
<222> LOCATION: (56)..(56)
<223> OTHER INFORMATION: Ile to Gly variant
<220> FEATURE:
<221> NAME/KEY: MISC_FEATURE
<222> LOCATION: (81)..(81)
<223> OTHER INFORMATION: Leu to Gly variant

<400> SEQUENCE: 8

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Tyr Thr Glu Arg Cys Gly Ser Gly
    50                  55                  60

Leu Arg Cys Gln Pro Ser Pro Asp Glu Ala Arg Pro Leu Gln Ala Leu
65                  70                  75                  80

Gly Asp Gly Arg Gly Leu Cys
                85

<210> SEQ ID NO 9
<211> LENGTH: 87
<212> TYPE: PRT
<213> ORGANISM: Homo sapiens
<220> FEATURE:
<221> NAME/KEY: MISC_FEATURE
<222> LOCATION: (80)..(80)
<223> OTHER INFORMATION: Leu to Gly variant
<220> FEATURE:
<221> NAME/KEY: MISC_FEATURE
<222> LOCATION: (81)..(81)
<223> OTHER INFORMATION: Leu to Gly variant

<400> SEQUENCE: 9

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Ile Tyr Thr Glu Arg Cys Gly Ser Gly
    50                  55                  60

Leu Arg Cys Gln Pro Ser Pro Asp Glu Ala Arg Pro Leu Gln Ala Gly
65                  70                  75                  80

Gly Asp Gly Arg Gly Leu Cys
                85

<210> SEQ ID NO 10
<211> LENGTH: 87
<212> TYPE: PRT
<213> ORGANISM: Homo sapiens
<220> FEATURE:
<221> NAME/KEY: MISC_FEATURE
<222> LOCATION: (56)..(56)
<223> OTHER INFORMATION: Ile to Gly variant
<220> FEATURE:
<221> NAME/KEY: MISC_FEATURE
<222> LOCATION: (80)..(80)
<223> OTHER INFORMATION: Leu to Gly variant
<220> FEATURE:
<221> NAME/KEY: MISC_FEATURE
<222> LOCATION: (81)..(81)
```

```
<223> OTHER INFORMATION: Leu to Gly variant

<400> SEQUENCE: 10

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20              25              30

Glu Leu Val Arg Glu Pro Gly Cys Gly Cys Cys Leu Thr Cys Ala Leu
            35              40              45

Ser Glu Gly Gln Pro Cys Gly Gly Tyr Thr Glu Arg Cys Gly Ser Gly
    50              55                  60

Leu Arg Cys Gln Pro Ser Pro Asp Glu Ala Arg Pro Leu Gln Ala Gly
65              70              75                  80

Gly Asp Gly Arg Gly Leu Cys
                85

<210> SEQ ID NO 11
<211> LENGTH: 87
<212> TYPE: PRT
<213> ORGANISM: Homo sapiens

<400> SEQUENCE: 11

Gly Ala Ser Ser Gly Gly Leu Gly Pro Val Val Arg Cys Glu Pro Cys
1               5                   10                  15

Asp Ala Arg Ala Leu Ala Gln Cys Ala Pro Pro Ala Val Cys Ala
            20              25              30

Glu Leu Val Arg Glu Pro Gly Cys Gly Cys Cys Leu Thr Cys Ala Leu
            35              40              45

Ser Glu Gly Gln Pro Cys Gly Ile Tyr Thr Glu Arg Cys Gly Ser Gly
    50              55                  60

Leu Arg Cys Gln Pro Ser Pro Asp Glu Ala Arg Pro Leu Gln Ala Leu
65              70              75                  80

Leu Asp Gly Arg Gly Leu Cys
                85
```